(12) United States Patent
Chi et al.

(10) Patent No.: US 11,512,041 B2
(45) Date of Patent: Nov. 29, 2022

(54) HIGHLY ENANTIOSELECTIVE ACCESS TO CYCLIC BETA-AMINO ACIDS

(71) Applicant: Nanyang Technological University, Singapore (SG)

(72) Inventors: Yonggui Chi, Singapore (SG); Zhijian Huang, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 17/112,486

(22) Filed: Dec. 4, 2020

(65) Prior Publication Data

US 2021/0171436 A1 Jun. 10, 2021

(30) Foreign Application Priority Data

Dec. 4, 2019 (SG) .......................... 10201911644V

(51) Int. Cl.
C07C 221/00 (2006.01)
C07B 51/00 (2006.01)
C07C 223/04 (2006.01)

(52) U.S. Cl.
CPC ............ *C07C 221/00* (2013.01); *C07B 51/00* (2013.01); *C07C 223/04* (2013.01)

(58) Field of Classification Search
None
See application file for complete search history.

(56) References Cited

U.S. PATENT DOCUMENTS 5,296,503 A  3/1994  Kunisch et al.

OTHER PUBLICATIONS

Chi, Y. et al. Agnew. Chem. Int. Ed. 2019, 58, 17189-17193.*
Chi, Y. et al. Agnew. Chem. Int. Ed. 2019, 58, 17189-17193 (supplemental data).*
V. Gupta, S. T. Mandal, C. Schneider, "Organocatalytic, Highly Enantioselective Vinylogous Mukaiyama-Michael Reaction of Acyclic Dienol Silyl Ethers" Angew. Chem. Int. Ed. 2012, 51, 12609-12612, DOI: 10.1002/anie.201207058.
S. Basu, V. Gupta, J. Nickel, C. Schneider, "Organocatalytic Enantioselective Vinylogous Michael Reaction of Vinylketene Silyl-N,O-Acetals" Org. Lett. 2014, 16, 274-277, DOI: 10 1021/ol403275k.
Y. Gu, Y. Wang, T.-Y. Yu, Y.-M. Liang, P.-F. Xu, "Rationally Designed Multifunctional Supramolecular Iminium Catalysis: Direct Vinylogous Michael Addition of Unmodified Linear Dienol Substrates" Angew. Chem. Int. Ed. 2014, 53, 14128-14131, DOI: 10.1002/anie.201406786.

(Continued)

*Primary Examiner* — Clinton A Brooks

(57) ABSTRACT

Disclosed herein is a method of forming a compound of formula I:

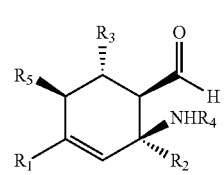

Figure 1A:
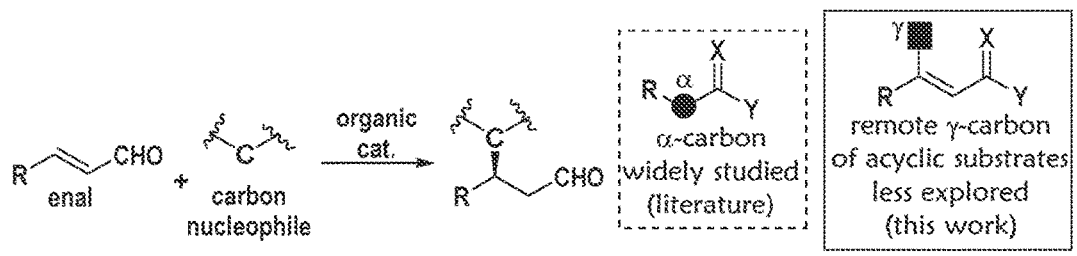

wherein the substituents are defined in the specification. In particular, the compounds of formula I can be converted to amino acids bearing quaternary stereocenters with exceptional optical purities.

19 Claims, 6 Drawing Sheets

(56) References Cited

OTHER PUBLICATIONS

Q. Guo, A. J. Fraboni, S. E. Brenner-Moyer, "Direct Diastereo- and Enantioselective Vinylogous Michael Additionsof Linear Enones" Org. Lett. 2016, 18, 2628-2631, DOI:10.1021/acs.orglett.6b01050.
A. Trojan, H. Beil, "Tilidine Abuse and Dependence" Drug Alcohol Depen. 1978, 3, 383-391.
T. Hashimoto, S. Kondo, T. Takita, M. Hamada, T. Takeuchi, Y. Okami, H. Umezawa, "Oryzoxymycin, A New Antibiotic" J. Antibiot. 1968, 21, 653-658.
F. Fülöp, "The Chemistry of 2-Aminocycloalkanecarboxylic Acids" Chem. Rev. 2001, 101, 2181-2204, DOI: 10.1021/cr000456z.
L. Kiss, F. Fulop, "Synthesis of Carbocyclic and Heterocyclic |3-Aminocarboxylic Acids" Chem. Rev. 2014, 114, 1116-1169.
M. Cheng et al., "CEP-28122, a Highly Potent and Selective Orally Active Inhibitor of Anaplastic Lymphoma Kinase with Antitumor Activity in Experimental Models of Human Cancers" Mol. Cancer Ther. 2012, 11, 670-679, doi:10.1158/1535-7163.
M. P. Clark et al., "Discovery of a Novel, First-in-Class, Orally Bioavailable Azaindole Inhibitor (VX-787) of Influenza PB2" J. Med. Chem. 2014, 57, 6668-6678.
L. L. Chang et al., "Highly constrained bicyclic VLA-4 antagonists" Bioorg. Med. Chem. Lett. 2007, 17, 597-601, doi:10.1016/j.bmcl. 2006.11.011.
T. Feng, Y. Li, Y.-Y. Wang, X.-H. Cai, Y.-P. Liu, X.-D. Luo, "Cytotoxic Indole Alkaloids from Melodinus tenuicaudatus" J. Nat. Prod. 2010, 73, 1075-1079, DOI: 10.1021/np100086x.
S. H. Gellman, "Foldamers: A Manifesto" Acc. Chem. Res. 1998, 31, 173-180.
R. P. Cheng, S. H. Gellman, W. F. DeGrado, "B-Peptides: From Structure to Function" Chem. Rev. 2001, 101, 3219-3232.
D. H. Appella, L. A. Christianson, D. A. Klein, D. R. Powell, X. Huang, J. J. Barchi, S. H. Gellman, "Residue-based control of helix shape in fl-peptide oligomers" Nature 1997, 387, 381-384.
D. H. Appella, L. A. Christianson, D. A. Klein, M. R. Richards, D. R. Powell, S. H. Gellman, "Synthesis and Structural Characterization of Helix-Forming,-Peptides: trans-2-Aminocyclopentanecarboxylic Acid Oligomers" J. Am. Chem. Soc., 1999, 121, 7574-7581.
E. A. Porter, X. Wang, H.-S. Lee, B. Weisblum, S. H. Gellman, "Non-haemolytic b-amino-acid oligomers" Nature, 2000, 404, 565.
M. Marigo, T. C. Wabnitz, D. Fielenbach, K. A. Jørgensen, "Enantioselective Organocatalyzed a Sulfenylationof Aldehydes" Angew. Chem. Int. Ed. 2005, 44, 794-797, DOI: 10.1002/anie. 200462101.
T. Fukuyama, C.-K, Jow, M. Cheung. "2- and 4-Nitrobenzenesulfonamides: Exceptionally Versatile Means for Preparation of Secondary Amines and Protection of Amines" Tetrahedron Lett. 1995, 36, 6373-6374.
A. Kessler, H. Faure, M. C. Roussanne, S. Ferry, M. Ruat, P. Dauban, R. H. Dodd, "N1-Arylsulfonyl-N2-(1-(1-naphthyl)ethyl)-1,2-diaminocyclohexanes: A New Classof Calcilytic Agents Acting at theCalcium-Sensing Receptor" ChemBioChem 2004, 5, 1131-1136, DOI: 10.1002/cbic.200400049.
"Protective Groups in Organic Chemistry", edited by J.W.F. McOmie, Plenum Press (1973).
Hidenori Shirakawa & Hiroshi Sano, "Proline-catalyzed asymmetric Diels-Alder reactions of an o-quinodimethane" Tetrahedron Letters 55 (2014) 4095-4097, http://dx.doi.org/10.1016/j.tetlet.2014. 05.107.
Hu, Z.; Liu, J.; Li, G.; Dong, Z.; Li W. "Synthesis of Asymmetric Triarylbenzenes by Using SOCl2—C2H50H Reagent" J. Chin Chem. Soc. 2004, 51, 581-583.
Ott, A. A.; Goshey, C. S.; Topczewski, J. J. "Dynamic Kinetic Resolution of Allylic Azides via Asymmetric Dihydroxylation" J. Am. Chem. Soc. 2017, 139, 7737, DOI:10.1021/jacs.7b04203.
Nishikawa, Y.; Yamamoto, H. "Iron-Catalyzed Asymmetric Epoxidation of β,β-Disubstituted Enones" J. Am. Chem. Soc. 2011, 133, 8432, DOI: 10.1021/ja201873d.
Guo, W.; Cheng, H.-G.; Chen, L.-Y.; Xuan, J.; Feng, Z.-J.; Chen, J.-R.; Lu, L.-Q.; Xiao, W.-J. "De Novo Synthesis of γ, γ-Disubstituted Butyrolactones through a Visible Light Photocatalytic Arylation-Lactonization Sequence" Adv. Synth. Catal. 2014, 356, 2787, DOI: 10.1002/adsc.201400041.
Jiang, K.; Tiwari, B.; Chi, Y. R. "Access to Spirocyclic Oxindoles via N-Heterocyclic Carbene-Catalyzed Reactions of Enals and Oxindole-Derived α,β-Unsaturated Imines" Org. Lett. 2012, 14, 2382, DOI: 10.1021/ol3008028.
Liu, S.; Liebeskind, L. S. "A Simple, Modular Synthesis of Substituted Pyridines" J. Am. Chem. Soc. 2008, 130, 6918, DOI:10. 1021/ja8013743.
Ortín, I.; Dixon, D. J. "Direct Catalytic Enantio- and Diastereoselective Mannich Reaction of Isocyanoacetates and Ketimines" Angew Chem. Int. Ed. 2014, 53, 3462, DOI: 10.1002/anie.201309719.
Jennings, W. B.; Lovely, C. J. "An Efficient Method for the Preparation of N-Phosphinoyl and N-!Sulphonyl Imines Direxxly From Aromatic Aldehydrs" Tetrahedron Lett. 1988, 29, 3752.
Y. Hayashi, H. Gotoh, T. Hayashi, M. Shoji, "Diphenylprolinol Silyl Ethers as Efficient Organocatalysts for the Asymmetric Michael Reaction of Aldehydes and Nitroalkenes" Angew. Chem. Int. Ed. 2005, 44, 4212-4215, DOI: 10.1002/anie.200500599.
Abiko, A.; Roberts, J. C.; Takemasa, T.; Masamune, S. "KMn04 REvisitied: Oxidation of Aldehydes to Carboxylic Acids in the tert-butyl Alcohol—Aqueous NaH2PO4 System" Tetrahedron Lett. 1986, 27, 4537.
Kessler, A.; Faure, H.; Roussanne, M. C.; Ferry, S.; Ruat, M.; Dauban, P.; Dodd, R. H. "N1-Arylsulfonyl-N2-(1-(1-naphthyl)ethyl)-1,2-diaminocyclohexanes: A New Class of Calcilytic Agents Acting at the Calcium-Sensing Receptor" ChemBioChem 2004, 5, 1131, DOI: 10.1002/cbic.200400049.
Takizawa, S.; Hirata, S.; Murai, K.; Fujioka, H.; Sasai, H. "C3-Symmetric chiral trisimidazoline-catalyzed Friedel-Crafts (FC)-type reaction" Org. Biomol. Chem. 2014, 12, 5827, DOI: 10.1039/c4ob00925h.
Philippe Duret, Bruno Figadere, Reynaid Hocquemiller, Andre Cave "Epimerization of Annonaceons Acetogenins under Basic Conditions" Tetrahedron Lett. 1997, 38, 8849-8852.
A. Erkkilä, I. Majander, P. M. Pihko, "Iminium Catalysis" Chem. Rev. 2007, 107, 5416-5470, DOI: 10.1021/cr068388p.
D. Enders, C. Grondal, M. R. M. Hüttl, "Asymmetric Organocatalytic Domino Reactions" Angew. Chem. Int. Ed. 2007, 46, 1570-1581, DOI: 10.1002/anie.200603129.
W. S. Jen, J. J. M. Wiener, D. W. C. MacMillan, "New Strategies for Organic Catalysis: The First Enantioselective Organocatalytic 1,3-DipolarCycloaddition" J. Am. Chem. Soc. 2000, 122, 9874-9875, DOI: 10.1021/ja005517p.
M. Marigo, T. Schulte, J. Franzen, K. A. Jørgensen, "Asymmetric Multicomponent Domino Reactions and Highly Enantioselective Conjugated Addition of Thiols to a,b-Unsaturated Aldehydes" J. Am. Chem. Soc. 2005, 127, 15710-15711, DOI: 10.1021/ja055291w.
D. Enders, M. R. M. Huttl, C. Grondal, G. Raabe, "Control of four stereocentres in a triple cascade organocatalytic reaction" Nature 2006, 441, 861-863, doi:10.1038/nature04820.
S. Mayer, B. List, "Asymmetric Counteranion-Directed Catalysis" Angew. Chem. Int. Ed. 2006, 45, 4193-4195, DOI: 10.1002/anie. 200600512.
X. Jiang, B. Tan, C. F. Barbas III, "Core-Structure-Motivated Design of Iminium-Enolate Organocascade Reactions: Enantioselective Syntheses of 5,6-Dihydroindolizines" Angew. Chem. Int. Ed. 2013, 52, 9261-9265, DOI: 10.1002/anie.201303300.
Q. Liu, L. Zu, "Organocatalytic Enantioselective Cross-Vinylogous Rauhut-Currier Reaction of Methyl Coumalate with Enals" Angew. Chem. Int. Ed. 2018, 57, 9505-9509, DOI:10.1002/anie.201805019.
M. N. Hopkinson, C. Richter, M. Schedler, F. Glorius, "An overview of N-heterocyclic carbenes" Nature 2014, 510, 485-496, doi:10.1038/nature13384.
D. M. Flanigan, F. Romanov-Michailidis, N. A. White, T. Rovis, "Organocatalytic Reactions Enabled by N-Heterocyclic Carbenes" Chem. Rev. 2015, 115, 9307-9387, DOI: 10.1021/acs.chemrev. 5b00060.
N. T. Reynolds, J. R. de Alaniz, T. Rovis, "Conversion of a-Haloaldehydes into Acylating Agents by an Internal Redox Reac-

(56) References Cited

OTHER PUBLICATIONS tion Catalyzed by Nucleophilic Carbenes" J Am. Chem. Soc. 2004, 126, 9518-9519, DOI: 10.1021/ja046991o.

M. He, J. R. Struble, J. W. Bode, "Highly Enantioselective Azadiene Diels-Alder Reactions Catalyzed by Chiral N-Heterocyclic Carbenes" J. Am. Chem. Soc. 2006, 128, 8418-8420, DOI: 10.1021/ja062707c.

D. Enders, O. Niemeier, T. Balensiefer, "Asymmetric Intramolecular Crossed-Benzoin Reactions by N-Heterocyclic Carbene Catalysis" Angew. Chem. Int. Ed. 2006, 45, 1463-146, DOI: 10.1002/anie.200503885.

D. E. A. Raup, B. Cardinal-David, D. Holte, K. A. Scheidt, "Cooperative catalysis by carbenes and Lewis acids in a highly stereoselective route to γ-lactams" Nat. Chem. 2010, 2, 766-771, DOI: 10.1038/NCHEM.727.

Z. Q. Fu, J. F. Xu, T. S. Zhu, W. W. Y. Leong, Y. R. Chi, "b-Carbon activation of saturated carboxylic estersthrough N-neterocyclic carbene organocatalysis" Nat. Chem. 2013, 5, 835-839, DOI: 10.1038/NCHEM.1710.

H. Lv, W.-Q. Jia, L.-H. Sun, S. Ye, "N-Heterocyclic Carbene Catalyzed [4+3] Annulation of Enals and o-Quinone Methides: Highly Enantioselective Synthesis of Benzo-e-Lactones" Angew. Chem. 2013, 125, 8769-8772; Angew. Chem. Int. Ed. 2013, 52, 8607-8610, DOI: 10.1002/anie.201303903.

A. Patra, S. Mukherjee, T. K. Das, S. Jain, R. G. Gonnade, A. T. Biju, "N-Heterocyclic-Carbene-Catalyzed Umpolung of mines" Angew. Chem. Int. Ed. 2017, 56, 2730-2734, DOI:10.1002/anie.201611268.

J. Guin, S. De Sarkar, S. Grimme, A. Studer, "Biomimetic Carbene-Catalyzed Oxidations of Aldehydes Using TEMPO" Angew. Chem. Int. Ed. 2008, 47, 8727-8730, DOI: 10.1002/anie.200802735.

A. G. Kravina, J. Mahatthananchai, J. W. Bode, "Enantioselective, NHC-Catalyzed Annulations of Trisubstituted Enalsand Cyclic N-Sulfonylimines via a,b-Unsaturated Acyl Azoliums" Angew. Chem. Int. Ed. 2012, 51, 9433-9436, DOI: 10.1002/anie.201204145.

J. Mo, L. Shen, Y. R. Chi, "Direct b-Activation of Saturated Aldehydes to Formal Michael Acceptors through Oxidative NHC Catalysis" Angew. Chem. Int. Ed. 2013, 52, 8588-8591, DOI: 10.1002/anie.201302152.

Z.-Q. Liang, D.-L. Wang, H.-M. Zhang, S. Ye, "Enantioselective Synthesis of Bicyclic δ-Lactones via N-Heterocyclic Carbene-Catalyzed Cascade Reaction" Org. Lett. 2015, 17, 5140-5143, DOI: 10.1021/acs.orglett.5b02695.

A. Carlone, M. Marigo, C. North, A. Landa, K. A. Jørgensen, "A simple asymmetric organocatalytic approach to optically active cyclohexenones" Chem. Commun. 2006, 4928-4930, DOI: 10.1039/b611366d.

C. Palomo, A. Landa, A. Mielgo, M. Oiarbide, A. Puente, S. Vera, "Water-Compatible Iminium Activation: Organocatalytic MichaelReactions of Carbon-Centered Nucleophiles with Enals" Angew. Chem. Int. Ed. 2007, 46, 8431-8435, DOI: 10.1002/anie.200703261.

Y. Hayashi, M. Toyoshima, H. Gotoh, H. Ishikawa, "Diphenylprolinol Silyl Ether Catalysis in an Asymmetric Formal Carbo [3+3] Cycloaddition Reaction via a Domino Michael/Knoevenagel Condensation" Org. Lett. 2009, 11, 45-48, DOI: 10.1021/ol802330h.

V. Blanco, D. A. Leith, U. Lewandowska, B. Lewandowski, V. Marcos, "Exploring the Activation Modes of a Rotaxane-Based Switchable Organocatalyst" J. Am. Chem. Soc. 2014, 136, 15775-15780, DOI: 0.1021/ja509236u.

S. Duce, I. Alonso, A. M. Lamsabhi, E. Rodrigo, S. Morales. J. L. G. Ruano, A. Poveda, P. Mauleón, M. B. Cid, "The Acidity of a Carbon Nucleophile Dictates Enantioselectivity and Reactivity in Michael Additions to Aromatic and Aliphatic Enals vialminium Activation" ACS Catal. 2018, 8, 22-34, DOI:10.1021/acscatal.7b02806.

C. Schneider, F. Abels, "Catalytic, enantioselective vinylogous Michael reactions" Org. Biomol. Chem. 2014, 12, 3531-3543, DOI: 10.1039/c4ob00332b.

Y. Yin, Z. Jiang, "Organocatalytic Asymmetric Vinylogous Michael Reactions" ChemCatChem 2017, 9, 4306-4318, DOI:10.1002/cctc.201700941.

X. Feng, H.-L. Cui, S. Xu, L. Wu, Y.-C. Chen, "Organocatalytic Direct Vinylogous Michael Addition of a,b-Unsaturatedg-Butyrolactam toa,b-Unsaturated Aldehydes and an Illustration to Scaffold Diversity Synthesis" Chem. Eur. J. 2010, 16, 10309-10312, DOI: 10.1002/chem.201001350.

A. Quintard, A. Lefranc, A. Alexakis, "Highly Enantioselective Direct Vinylogous Michael Addition of γ-Butenolide to Enals" Org. Lett. 2011, 13, 1540-1543, DOI: 10.1021/01200235j.

L. Dell'Amico, L. Albrecht, T. Naicker, P. H. Poulsen, K. A. Jorgensen, "Beyond Classical Reactivity Patterns: Shifting from 1,4- to 1,6-Additions in Regio- and Enantioselective Organocatalyzed Vinylogous Reactions of Olefinic Lactones with Enals and 2,4-Dienals" J. Am. Chem. Soc. 2013, 135, 8063-8070, DOI: 0.1021/ja4029928.

L. Dell'Amico, G. Rassu, V. Zambrano, A. Sartori, C. Curti, L. Battistini, G. Pelosi, G. Casiraghi, F. Zanardi, "Exploring the Vinylogous Reactivity of Cyclohexenylidene Malononitriles: Switchable Regioselectivity in the Organocatalytic Asymmetric Addition to Enals Giving Highly Enantioenriched Carbabicyclic Structures" J. Am. Chem. Soc. 2014, 136, 11107-11114, DOI: 10.1021/ja5054576.

S. R. Yetra, S. Mondal, S. Mukherjee, R. G. Gonnade, A. T. Biju, "Enantioselective Synthesis of Spirocyclohexadienones by NHC-Catalyzed Formal [3++3] Annulation Reaction of Enals" Angew. Chem. Int. Ed. 2016, 55, 268-272, DOI: 10.1002/anie.201507802.

Z.-L. Jia, Y. Wang, C.-G. Zhao, X.-H. Zhang, P.-F. Xu, "Highly Enantioselective Construction of Hajos-Wiechert KetoneSkeletons via an Organocatalytic Vinylogous Michael/Stetter Relay Sequence" Org. Lett. 2017, 19, 2130-2133, DOI:10.1021/acs.orglett.7b00767.

S. P. Brown, N. C. Goodwin, D. W. C. MacMillan, "The First Enantioselective Organocatalytic Mukaiyama-Michael Reaction: A Direct Method for the Synthesis of Enantioenriched γ-Butenolide Architecture" J. Am. Chem. Soc. 2003, 125, 1192-1194, DOI: 10.1021/ja029095q.

Y. Huang, A. M. Walji, C. H. Larsen, D. W. C. MacMillan, "Enantioselective Organo-Cascade Catalysis" J. Am. Chem. Soc. 2005, 127, 15051-15053, DOI: 10.1021/ja055545d.

S. J. Ryan, L. Candish, D. W. Lupton, "N-Heterocyclic Carbene-Catalyzed (4p2) Cycloaddition/Decarboxylation of Silyl Dienol Ethers withr, β-Unsaturated Acid Fluorides" J. Am. Chem. Soc. 2011, 133, 4694-4697, DOI: /10.1021/ja111067.

\* cited by examiner

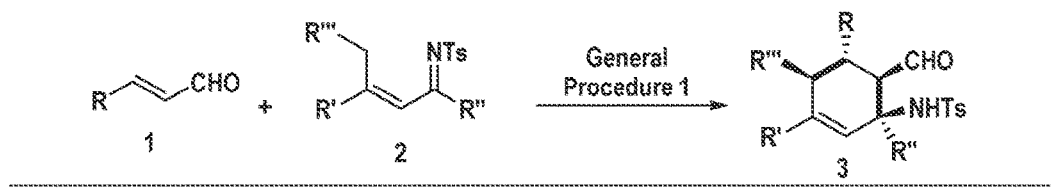
Fig. 2A
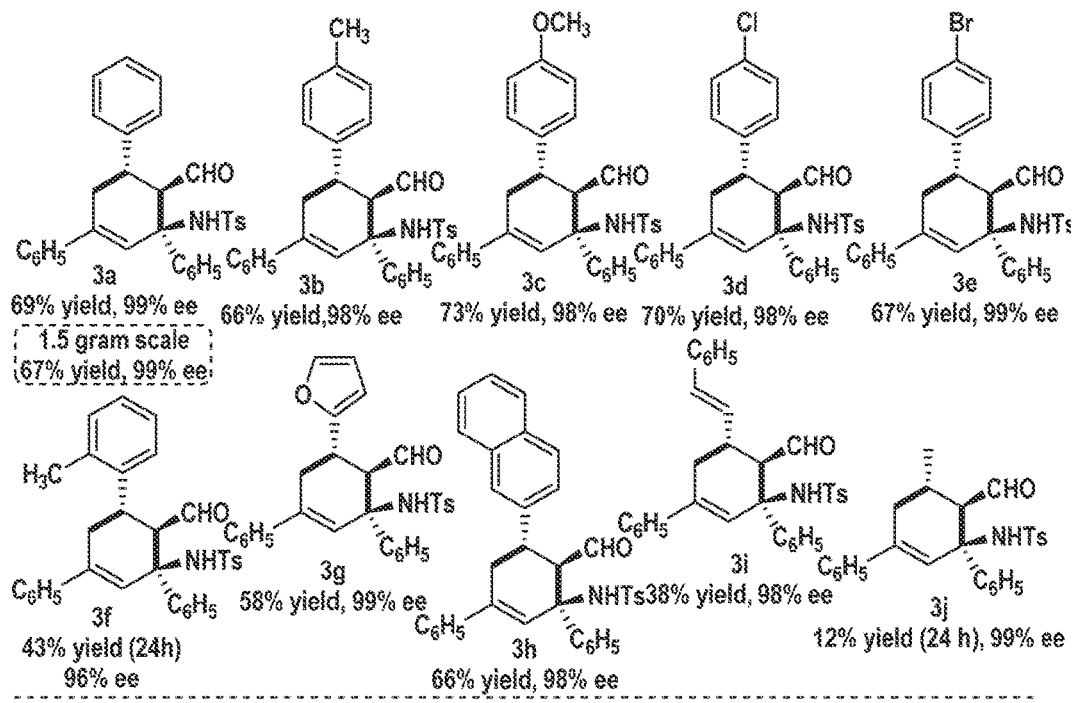
Fig. 2B
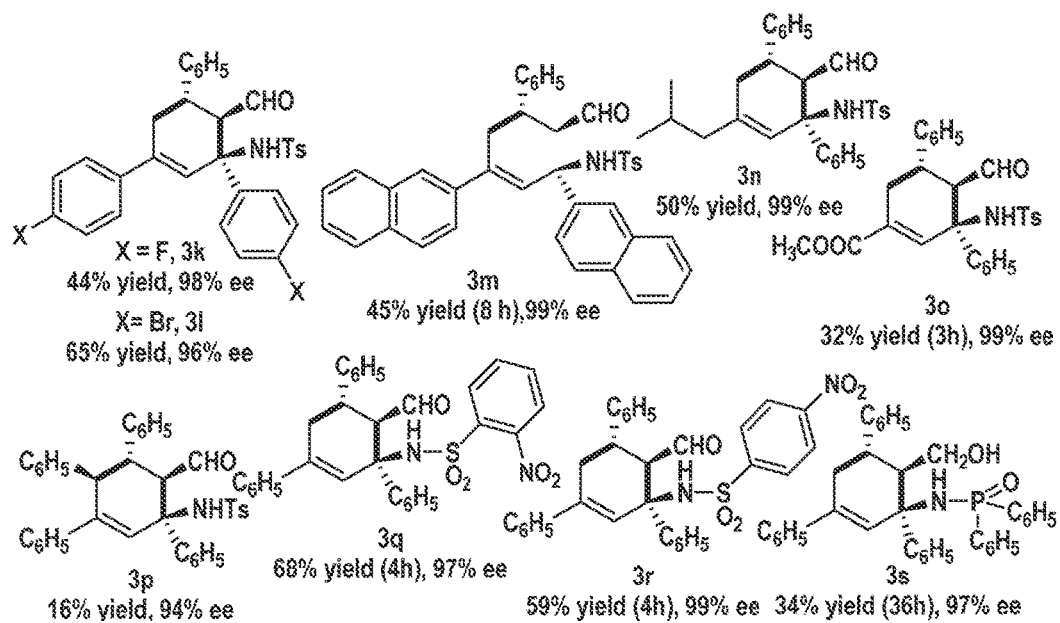

X-ray structure of 3a

HIGHLY ENANTIOSELECTIVE ACCESS TO CYCLIC BETA-AMINO ACIDS

CROSS-REFERENCE TO RELATED APPLICATIONS

The present application claims priority to Singapore Application No. SG 10201911644V filed with the Intellectual Property Office of Singapore on Dec. 4, 2019 which is incorporated herein by reference in its entirety for all purposes.

FIELD OF INVENTION

The invention relates to a method of forming cyclic β-amino aldehydes, which can be readily transformed to cyclic β-amino acids.

BACKGROUND

The listing or discussion of a prior-published document in this specification should not necessarily be taken as an acknowledgement that the document is part of the state of the art or is common general knowledge.

The addition of carbon nucleophiles to electron-deficient alkenes is a common strategy to form new carbon-carbon bonds. Amongst the classes of electron-deficient alkenes, α,β-unsaturated aldehydes (enals) can be readily activated by organic catalysts for asymmetric reactions with various nucleophiles. For example, reactions of enals with primary or secondary amine catalysts form α,β-unsaturated iminium intermediates that can undergo addition reactions with carbon or heteroatom nucleophiles. With N-heterocyclic carbenes (NHCs) as organic catalysts, in the presence of oxidants, enals can be converted to α,β-unsaturated azolium ester intermediates for further reactions. The majority of the carbon nucleophiles in organic catalytic 1,4-addition to enals (and related electron-deficient alkenes) are the α-carbon atoms of carbonyl compounds or their derivatives and analogues (FIG. 1(A)). Vinylogous Michael donors have also found use in the construction of C—C bonds at the γ-carbon centers of carbonyl compounds or their derivatives and analogues. However, most vinylogous Michael donors are restricted to cyclic substrates with at least one of the electron-rich double bonds incorporated in the ring systems. The use of acyclic linear vinylogous Michael donors in asymmetric addition to enals (via α,β-unsaturated iminium or azolium ester intermediates) remains less explored (FIG. 1(A)).

Figure 1B:
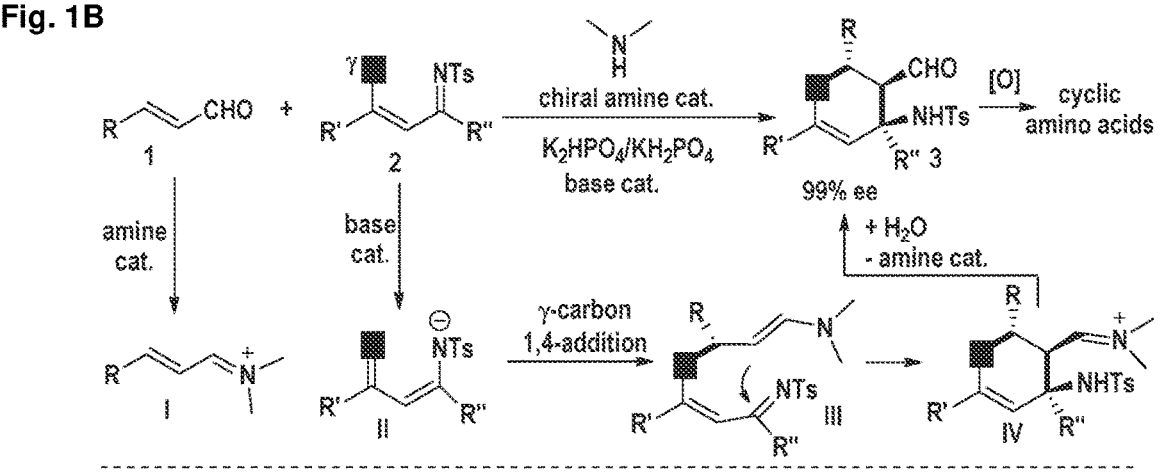
Figure 1C:
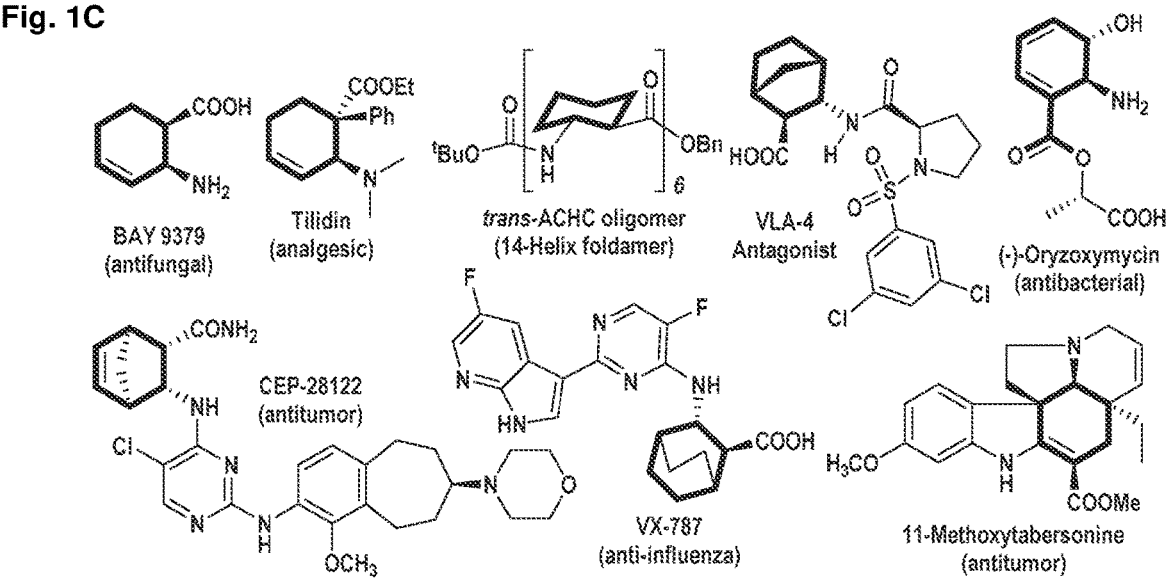

Cyclic amino acids (such as 6-membered cyclic β-amino acid BAY 9379, Tilidin, and oryzoxymycin) exhibit medicinally significant bioactivities (FIG. 1(C)). These amino acids are also key components in many pharmaceutical leads such as CEP-28122, VX-787, VLA-4 Antagonist and 11-methoxytabersonine. In the field of foldamers research, Gellman and co-workers have pioneered the creation of new peptidic structures by employing cyclic non-natural amino acids that include six-membered β-amino acids. There is therefore a need for an improved and efficient method for forming this class of cyclic β-amino acids which address the issues mentioned above.

SUMMARY OF INVENTION

It has been surprisingly found that it is possible to synthesise enantiomerically enriched cyclic β-amino aldehydes in one step from acyclic starting materials that can then be conveniently converted into a β-amino acid. Said method involves addition of the remote γ-carbon atoms of α,β-unsaturated imines to enals through use of an organic catalytic species. This highly chemo- and stereo-selective reaction affords cyclic β-amino aldehydes that can be converted to amino acids bearing quaternary stereocenters with exceptional optical purities.

Aspects and embodiments of the current invention will now be described by reference to the following numbered clauses.

1. A method of forming a compound of formula I:

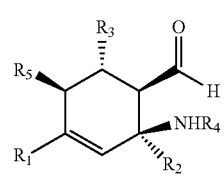

where:

$R_1$ and $R_2$ each independently represent $R_{6a}OC(O)$—, $C_1$ to $C_{10}$ alkyl, a carbocyclic ring system, and a heterocyclic ring system, where the $C_1$ to $C_{10}$ alkyl, carbocyclic ring system and heterocyclic ring system are unsubstituted or substituted by one or more substituents selected from the group consisting of halo, $OR_{7a}$, aryl, $Het^a$, and $C_1$ to $C_6$ alkyl, which $C_1$ to $C_6$ alkyl and aryl are unsubstituted or substituted by one or more halo groups;

$R_3$ represents $C_1$ to $C_{10}$ alkyl, $C_2$ to $C_{10}$ alkenyl, a carbocyclic ring system, and a heterocyclic ring system, where the $C_1$ to $C_{10}$ alkyl, $C_2$ to $C_{10}$ alkenyl, carbocyclic ring system and heterocyclic ring system are unsubstituted or substituted by one or more substituents selected from the group consisting of halo, $OR_{7b}$, aryl, $Het^b$, and $C_1$ to $C_6$ alkyl, which $C_1$ to $C_6$ alkyl and aryl are unsubstituted or substituted by one or more halo groups;

$R_4$ represents a nitrogen protecting group;

$R_5$ represents H, $R_{6b}OC(O)$—, $C_1$ to $C_{10}$ alkyl, a carbocyclic ring system, and a heterocyclic ring system, where the $C_1$ to $C_{10}$ alkyl, carbocyclic ring system and heterocyclic ring system are unsubstituted or substituted by one or more substituents selected from the group consisting of halo, $OR_{7c}$, aryl, $Het^c$, and $C_1$ to $C_6$ alkyl, which $C_1$ to $C_6$ alkyl and aryl are unsubstituted or substituted by one or more halo groups;

$Het^a$ to $Het^c$ are each independently a 4- to 14-membered heterocyclic ring system that is unsubstituted or substituted with one or more substituents selected from halo and $C_1$ to $C_6$ alkyl, which is unsubstituted or substituted by one or more halo groups;

$R_{6a}$ and $R_{6b}$ and $R_{7a}$ to $R_{7c}$ are each independently $C_1$ to $C_{10}$ alkyl that is unsubstituted or substituted by one or more halo groups;

comprising the steps of reacting a compound of formula II:

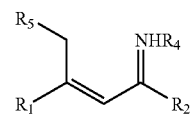

where $R_1$, $R_2$, $R_4$ and $R_5$ are as defined above, with a compound of formula III:

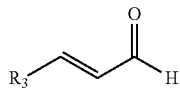

where $R_3$ is as defined above, in the presence of a solvent, a base comprising $KH_2PO_4$, and a catalyst of formula IV:

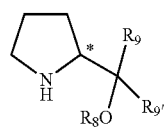

where:
the * represents a chiral centre;
$R_8$ is a protecting group for OH; and
$R_9$ and $R_{9'}$ each independently represent an aryl group that is unsubstituted or substituted by one or more groups selected from halo, $C_1$ to $C_6$ alkyl, phenyl, and naphthyl, where the $C_1$ to $C_6$ alkyl, phenyl and naphthyl are unsubstituted or substituted by one or more halo groups, optionally wherein $R_9$ and $R_{9'}$ are identical.

2. The method according to Clause 1, wherein $R_1$ and $R_2$ each independently represent $R_{6a}OC(O)—$, $C_1$ to $C_6$ alkyl, phenyl, and naphthyl, where the $C_1$ to $C_6$ alkyl, phenyl, and naphthyl are unsubstituted or substituted by one or more substituents selected from the group consisting of halo and $C_1$ to $C_3$ alkyl, which $C_1$ to $C_3$ alkyl is unsubstituted or substituted by one or more halo groups.

3. The method according to Clause 1, wherein $R_5$ represents H, $C_1$ to $C_6$ alkyl, and phenyl, where the $C_1$ to $C_6$ alkyl and phenyl are unsubstituted or substituted by one or more substituents selected from the group consisting of halo and $C_1$ to $C_3$ alkyl, which $C_1$ to $C_3$ alkyl is unsubstituted or substituted by one or more halo groups.

4. The method according to Clause 1, wherein $R_3$ represents $C_1$ to $C_6$ alkyl, $C_2$ to $C_6$ alkenyl, phenyl, naphthyl and furanyl, where the $C_1$ to $C_6$ alkyl, $C_2$ to $C_6$ alkenyl, phenyl, naphthyl and furanyl are unsubstituted or substituted by one or more substituents selected from the group consisting of halo, phenyl, $OC_1$ to $C_3$ alkyl and $C_1$ to $C_3$ alkyl, which phenyl, $OC_1$ to $C_3$ alkyl and $C_1$ to $C_3$ alkyl are unsubstituted or substituted by one or more halo groups.

5. The method according to Clause 1, wherein $R_4$ is selected from a tosyl group, a nosyl group, and a diphenylphosphinyl group and suitable isomers thereof.

6. The method according to Clause 1, wherein $R_{6a}$ and $R_{6b}$ and $R_{7a}$ to $R_{7c}$ are each independently $C_1$ to $C_3$ alkyl that is unsubstituted or substituted by one or more halo groups.

7. The method according to Clause 1, wherein the catalyst of formula IV is:

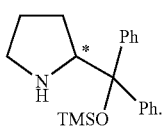

8. The method according to Clause 1, wherein the base further comprises a further base selected from one or more of the group consisting of $K_2HPO_4$, an amine base, and $Na_2HPO_4$.

9. The method according to Clause 8, wherein the amine base is selected from one or more of the group consisting of $Et_3N$, DMAP, and DABCO.

10. The method according to Clause 1, wherein the reaction is conducted in the presence of an additive selected from one or more of the group consisting of LiBr, NaCl, KCl, and $MgCl_2$.

11. The method according to Clause 10, wherein the additive is NaCl.

12. The method according to Clause 1, wherein the solvent consists essentially of an alkyl alcohol and water.

13. The method according to Clause 12, wherein the solvent is methanol and water.

14. The method according to Clause 12, wherein the alkyl alcohol:water volume:volume ratio is from 90:10 to 99.5:0.5.

15. The method according to Clause 14, wherein the alkyl alcohol:water volume:volume ratio is 99:1.

16. The method according to Clause 1, wherein one or both of the following apply:
(a) the reaction is conducted at a temperature of from 40 to 80° C.; and
(b) the reaction time is from 6 to 24 hours.

17. The method according to Clause 1, wherein one or more of the following apply:
(a) a molar ratio of the compound of formula III to the compound of formula II is from 1.1:1 to 4:1;
(b) a molar ratio of $KH_2PO_4$ to the compound of formula II is from 0.1:1 to 5:1, such as from 0.35:1 to 2:1 such as 1:1; and
(c) a molar ratio of the catalyst of formula IV to the compound of formula II is from 0.2:1 to 0.4:1.

18. The method according to Clause 8, wherein a total molar ratio of the base comprising $KH_2PO_4$ and a further base relative to the compound of formula II is from 1.5:1 to 2:1, where the $KH_2PO_4$ and the further base have a molar ratio of 1:1.

19. The method according to Clause 10, wherein a molar ratio of the additive to the compound of formula II is about 1:1.

DRAWINGS

Certain embodiments of the present disclosure are described more fully hereinafter with reference to the accompanying drawings.

FIG. 1A Known reaction scheme depicting organic catalytic 1,4-addition of carbon nucleophiles to enals; FIG. 1B Reaction scheme depicting addition of remote γ-carbon atoms of α,β-unsaturated imines to enals; FIG. 1C Examples of bioactive molecules and peptidic foldamers containing cyclic β-amino acids.

FIGS. 2A and 2B. Compounds formed in Example 2 by reacting (A) a variety of enals with 2a as imine substrate and (B) a variety of imines with 1a as enal substrate.

Figure 3:
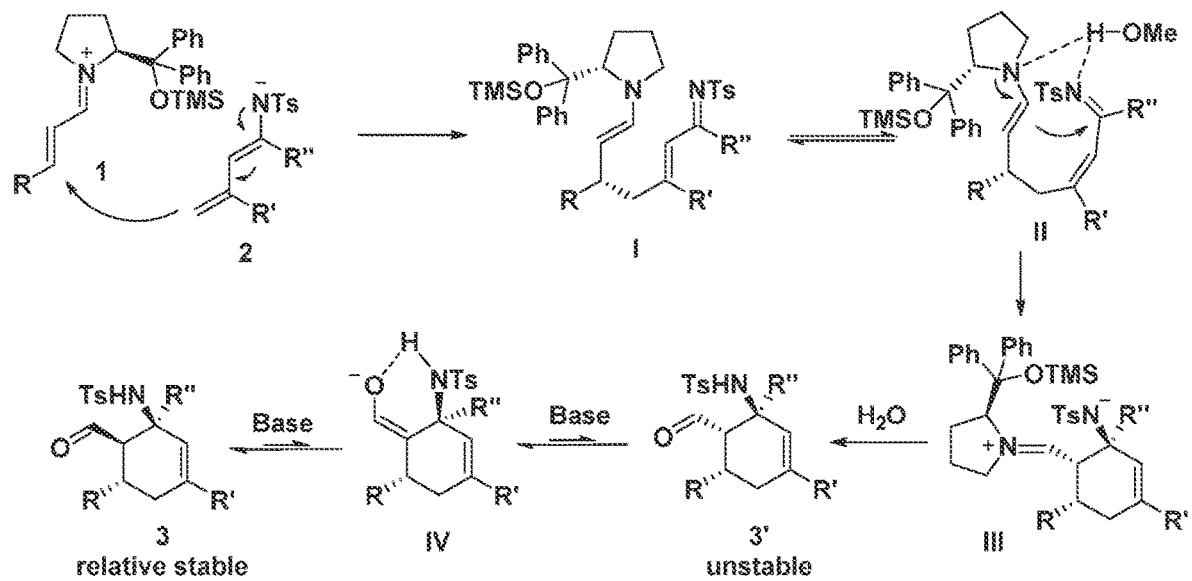

FIG. 3. Proposed mechanism for the generation of the cis-Mannich products.

Figure 4:
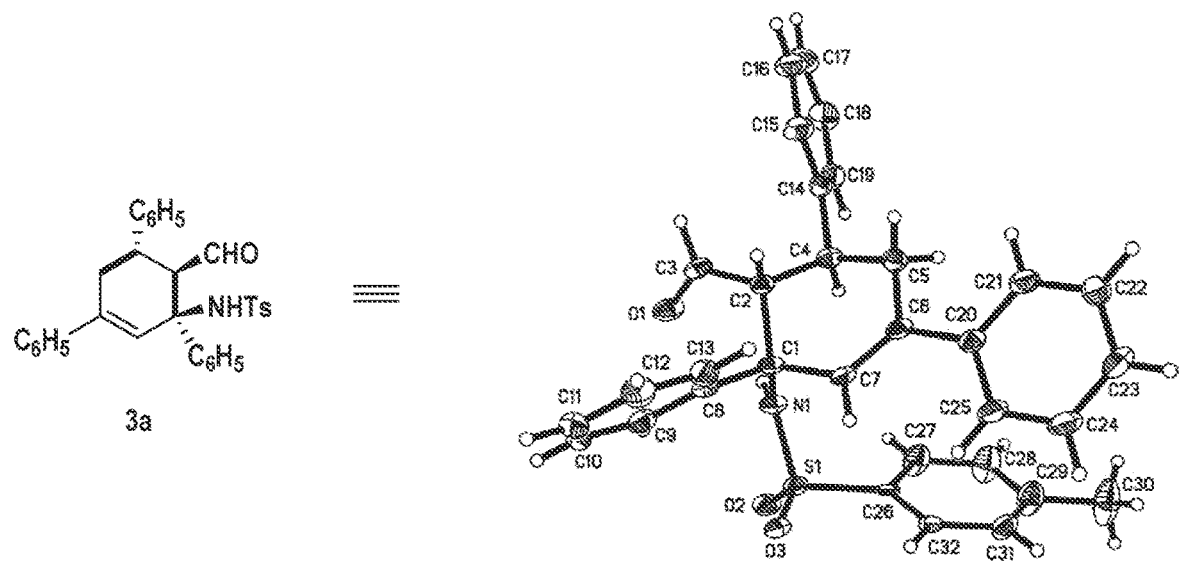

FIG. 4. X-ray structure of compound 3a

Figure 5:
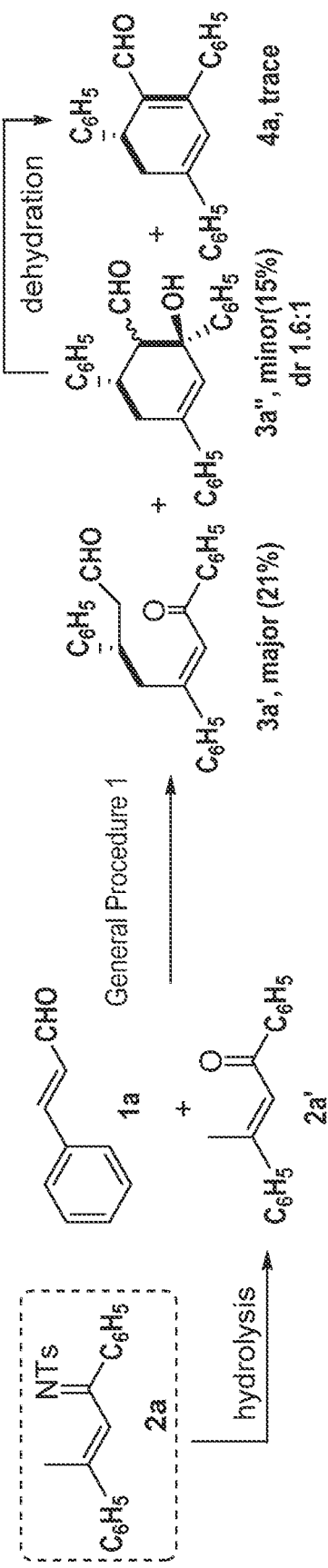

FIG. 5. Reaction scheme showing reaction of enone 2a' with enal 1a following General Procedure 1.

Figure 6:
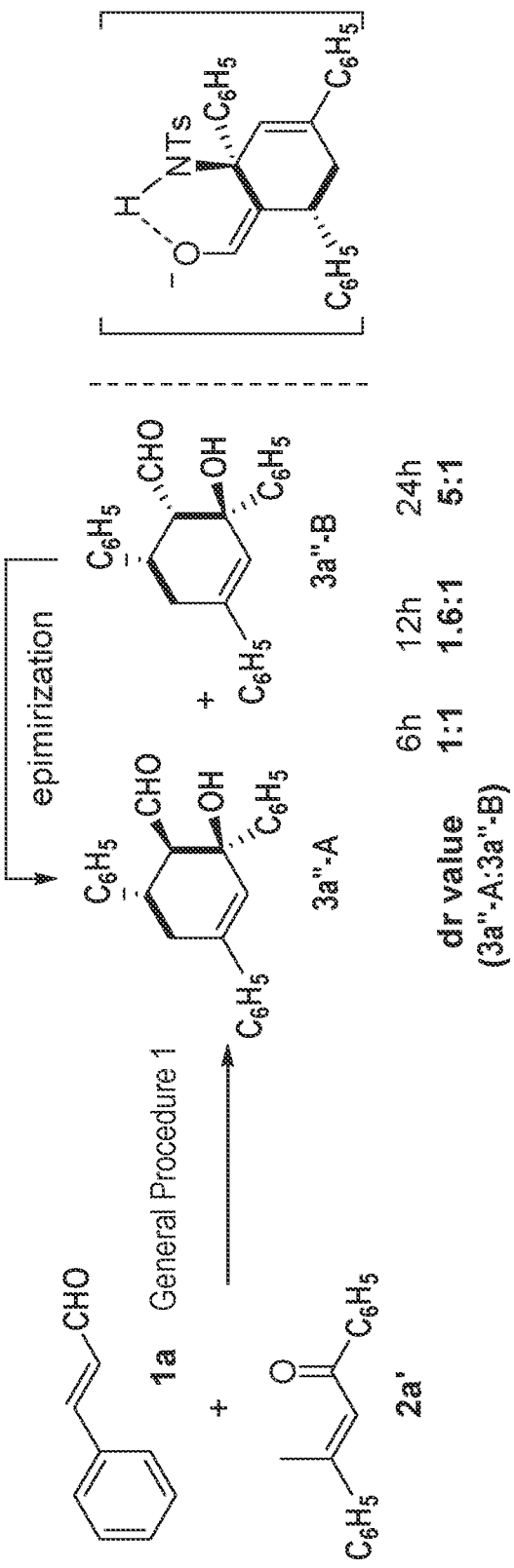

FIG. 6. Reaction scheme showing the effect of reaction time on transformation of 3a"-A from diastereoisomer 3a"-B.

Figure 7:
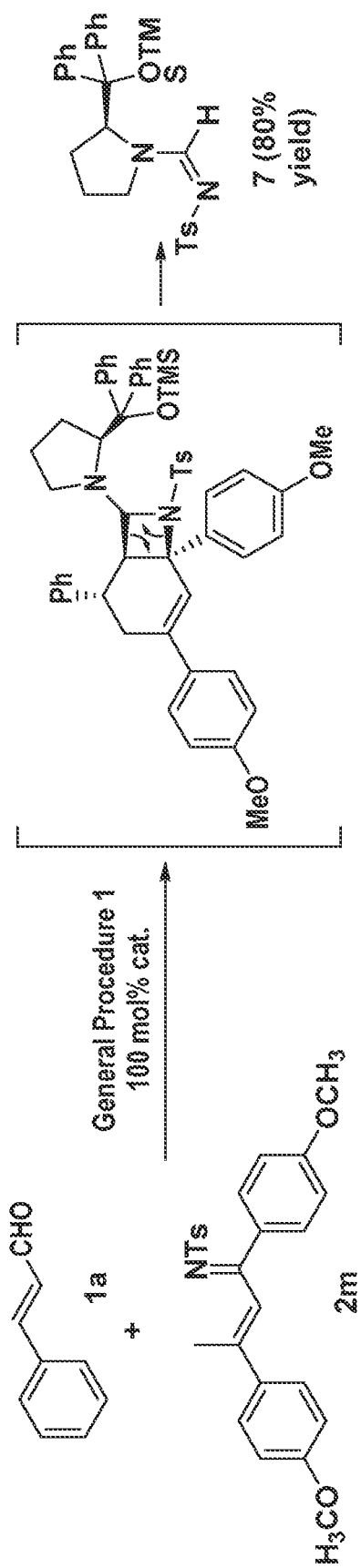

FIG. 7. Reaction scheme showing reaction of imine 2m with enal 1a following General Procedure 1 with 100 mol % catalyst.

DESCRIPTION

As noted above, the current invention relates to the reaction of α,β-unsaturated imines with an enal to provide a cyclic β-amino aldehyde. Thus, in a first aspect of the invention, there is provided a method of forming a compound of formula I:

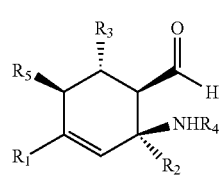

where:

$R_1$ and $R_2$ each independently represent $R_{6a}OC(O)$—, $C_1$ to $C_{10}$ alkyl, a carbocyclic ring system, and a heterocyclic ring system, where the $C_1$ to $C_{10}$ alkyl, carbocyclic ring system and heterocyclic ring system are unsubstituted or substituted by one or more substituents selected from the group consisting of halo, $OR_{7a}$, aryl, $Het^a$, and $C_1$ to $C_6$ alkyl, which $C_1$ to $C_6$ alkyl and aryl are unsubstituted or substituted by one or more halo groups;

$R_3$ represents $C_1$ to $C_{10}$ alkyl, $C_2$ to $C_{10}$ alkenyl, a carbocyclic ring system, and a heterocyclic ring system, where the $C_1$ to $C_{10}$ alkyl, $C_2$ to $C_{10}$ alkenyl, carbocyclic ring system and heterocyclic ring system are unsubstituted or substituted by one or more substituents selected from the group consisting of halo, $OR_7b$, aryl, $Het^b$, and $C_1$ to $C_6$ alkyl, which $C_1$ to $C_6$ alkyl and aryl are unsubstituted or substituted by one or more halo groups;

$R_4$ represents a nitrogen protecting group;

$R_5$ represents H, $R_{6b}OC(O)$—, $C_1$ to $C_{10}$ alkyl, a carbocyclic ring system, and a heterocyclic ring system, where the $C_1$ to $C_{10}$ alkyl, carbocyclic ring system and heterocyclic ring system are unsubstituted or substituted by one or more substituents selected from the group consisting of halo, $OR_{7c}$, aryl, $Het^c$, and $C_1$ to $C_6$ alkyl, which $C_1$ to $C_6$ alkyl and aryl are unsubstituted or substituted by one or more halo groups;

$Het^a$ to $Het^c$ are each independently a 4- to 14-membered heterocyclic ring system that is unsubstituted or substituted with one or more substituents selected from halo and $C_1$ to $C_6$ alkyl, which is unsubstituted or substituted by one or more halo groups;

$R_{6a}$ and $R_{6b}$ and $R_{7a}$ to $R_{7c}$ are each independently $C_1$ to $C_{10}$ alkyl that is unsubstituted or substituted by one or more halo groups;

comprising the steps of reacting a compound of formula II:

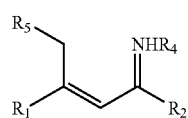

where $R_1$, $R_2$, $R_4$ and $R_5$ are as defined above, with a compound of formula III:

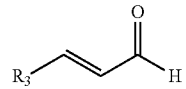

where $R_3$ is as defined above, in the presence of a solvent, a base comprising $KH_2PO_4$, and a catalyst of formula IV:

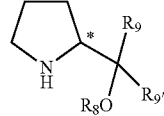

where:
the * represents a chiral centre;
$R_8$ is a protecting group for OH; and
$R_9$ and $R_{9'}$ each independently represent an aryl group that is unsubstituted or substituted by one or more groups selected from halo, $C_1$ to $C_6$ alkyl, phenyl, and naphthyl, where the $C_1$ to $C_6$ alkyl, phenyl and naphthyl are unsubstituted or substituted by one or more halo groups, optionally wherein $R_9$ and $R_{9'}$ are identical.

For the avoidance of doubt, the visual representation of the compound of formula I (and the other compounds mentioned herein) is intended to describe the relative stereochemical relationship of the substituents, not the absolute stereochemistry. Thus, the compound of formula I is intended to cover compounds having the following stereochemistry.

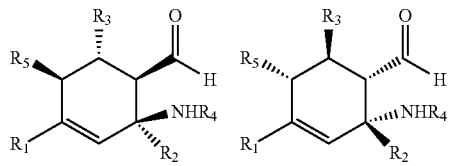

This is the case for all compounds described herein unless explicitly stated otherwise (e.g. for the specific compounds disclosed herein that have an absolute stereochemistry assigned to each stereocentre (i.e. R- or S-)).

References herein (in any aspect or embodiment of the invention) to compounds of formula I include references to such compounds perse, and to tautomers of such compounds.

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may contain one or more asymmetric carbon atoms and may therefore exhibit optical isomerism and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or high-performance liquid chromatography (HPLC), techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The term "halo" or "halo group", when used herein, includes references to fluoro, chloro, bromo and iodo.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Unless otherwise stated, the term "alkyl" refers to an unbranched or branched, acyclic saturated hydrocarbyl radical, which may be unsubstituted or substituted (with, for example, one or more halo atoms). The term "alkyl" is preferably $C_{1-10}$ alkyl and, more preferably, $C_{1-6}$ alkyl (such as ethyl, propyl, (e.g. n-propyl or isopropyl), butyl (e.g. branched or unbranched butyl), pentyl or, more preferably, methyl).

Unless otherwise stated, the term "alkenyl" refers to an unbranched or branched, acyclic unsaturated hydrocarbyl radical, which may be unsubstituted or substituted (with, for example, one or more halo atoms). The term "alkenyl" is preferably $C_{2-10}$ alkenyl and, more preferably, $C_{2-6}$ alkenyl (such as ethenyl, propenyl, (e.g. n-propenyl or isopropenyl), and butenyl (e.g. branched or unbranched butenyl), or pentenyl).

Unless otherwise specified herein, a "heterocyclic ring system" may be a 4- to 14-membered, such as a 5- to 10-membered (e.g. 6- to 10-membered), heterocyclic group that may be aromatic, fully saturated or partially unsaturated, and which contains one or more heteroatoms selected from O, S and N, which heterocyclic group may comprise one to three rings. Examples of heterocyclic ring systems that may be mentioned herein include, but are not limited to azetidinyl, dihydrofuranyl (e.g. 2,3-dihydrofuranyl, 2,5-dihydrofuranyl), dihydropyranyl (e.g. 3,4-dihydropyranyl, 3,6-dihydropyranyl), 4,5-dihydro-1H-maleimido, dioxanyl, dioxolanyl, furanyl, furazanyl, hexahydropyrimidinyl, hydantoinyl, imidazolyl, isothiazolyl, isoxazolidinyl, isoxazolyl, morpholinyl, 1,2- or 1,3-oxazinanyl, oxazolidinyl, oxazolyl, piperidinyl, piperazinyl, pyranyl, pyrazinyl, pyridazinyl, pyrazolyl, pyridinyl, pyrimidinyl, pyrrolinyl (e.g. 3-pyrrolinyl), pyrrolyl, pyrrolidinyl, pyrrolidinonyl, 3-sulfolenyl, sulfolanyl, tetrahydrofuranyl, tetrahydropyranyl, tetrahydropyridinyl (e.g. 3,4,5,6-tetrahydropyridinyl), 1,2,3,4-tetrahydropyrimidinyl, 3,4,5,6-tetrahydropyrimidinyl, tetrahydrothiophenyl, tetramethylenesulfoxide, tetrazolyl, thiadiazolyl, thiazolyl, thiazolidinyl, thienyl, thiophenethyl, triazolyl and triazinanyl.

When the heterocyclic ring system is aromatic, the heterocyclic ring system may be a heteroaryl group. The term "heteroaryl" when used herein refers to an aromatic group containing one or more heteroatom(s) (e.g. one to four heteroatoms) preferably selected from N, O and S (so forming, for example, a mono-, bi-, or tricyclic heteroaromatic group). Heteroaryl groups include those which have between 5 and 14 (e.g. 10) members and may be monocyclic, bicyclic or tricyclic, provided that at least one of the rings is aromatic. However, when heteroaryl groups are bicyclic or tricyclic, they are linked to the rest of the molecule via an aromatic ring. Heteroaryl groups that may be mentioned include benzothiadiazolyl (including 2,1,3-benzothiadiazolyl), isothiochromanyl and, more preferably, acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Particularly preferred heteroaryl groups include pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, thiophenetyl, thiophenyl, pyranyl, carbazolyl, acridinyl, quinolinyl, benzoimidazolyl, benzthiazolyl, purinyl, cinnolinyl and pterdinyl. Particularly preferred heteroaryl groups include monocylic heteroaryl groups such as furanyl.

In embodiments of the invention that may be mentioned herein, one or more of the following may apply:

(a) $R_1$ and $R_2$ may each independently represent $R_{6a}OC(O)$—, $C_1$ to $C_6$ alkyl, phenyl, and naphthyl, where the $C_1$ to $C_6$ alkyl, phenyl, and naphthyl are unsubstituted or substituted by one or more substituents selected from the group consisting of halo and $C_1$ to $C_3$ alkyl, which $C_1$ to $C_3$ alkyl is unsubstituted or substituted by one or more halo groups;

(b) $R_5$ may represent H, $C_1$ to $C_6$ alkyl, and phenyl, where the $C_1$ to $C_6$ alkyl and phenyl are unsubstituted or substituted by one or more substituents selected from the group consisting of halo and $C_1$ to $C_3$ alkyl, which $C_1$ to $C_3$ alkyl is unsubstituted or substituted by one or more halo groups;

(c) $R_3$ may represent $C_1$ to $C_6$ alkyl, $C_2$ to $C_6$ alkenyl, phenyl, naphthyl and furanyl, where the $C_1$ to $C_6$ alkyl, $C_2$ to $C_6$ alkenyl, phenyl, naphthyl and furanyl are unsubstituted or substituted by one or more substituents selected from the group consisting of halo, phenyl, $OC_1$ to $C_3$ alkyl and $C_1$ to $C_3$ alkyl, which phenyl, to $C_3$ alkyl and $C_1$ to $C_3$ alkyl are unsubstituted or substituted by one or more halo groups;

(d) $R_{6a}$ and $R_{6b}$ and $R_{7a}$ to $R_{7c}$ may each independently represent a $C_1$ to $C_3$ alkyl that is unsubstituted or substituted by one or more halo groups.

In embodiments of the invention where one or both of $R_1$ and $R_2$ represent phenyl, the phenyl group may not be substituted with electron donating groups such as alkyl (e.g. $C_1$ alkyl) and alkoxyl groups (e.g. —$OCH_3$). Without wishing to be bound by theory, it is believed that the use of a compound of formula (II) having these substituents in the reaction may deactivate the catalyst. This is demonstrated in Example 7.

Unless otherwise specified herein, a "carbocyclic ring system" may be a 4- to 14-membered, such as a 5- to 10-membered (e.g. 6- to 10-membered, such as 6-membered or 10-membered), carbocyclic group that may be aromatic, fully saturated or partially unsaturated, which carbocyclic group may comprise one or two rings. Examples of carbocyclic ring systems that may be mentioned herein include, but are not limited to cyclobutyl, cyclopentyl, cyclohexyl, cyclooctyl, phenyl, naphthyl, decalinyl, tetralinyl, bicyclo[4.2.0]octanyl, and 2,3,3a,4,5,6,7,7a-octahydro-1H-indanyl. Particularly preferred carbocyclic groups include phenyl, cyclohexyl and naphthyl.

In the processes described above and hereinafter, certain functional groups of the compound of formula I and the starting materials used to make it may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wuts, Wiley-Interscience (1999).

As used herein, the term "functional groups" means, in the case of unprotected functional groups, hydroxy-, thiolo-, amino-, carboxylic acid and, in the case of protected functional groups, lower alkoxy, N-, O-, S-acetyl, carboxylic acid ester. When used herein, "lower alkoxy" refers to a $C_1$ to $C_4$ alkyl group attached to an oxygen atom, such as methyl, ethyl, n-propyl, isopropyl, n-butyl, sec-butyl and tert-butyl (e.g. methyl).

As noted above, the group $R_4$ may be a nitrogen protecting group. Any suitable nitrogen protecting group may be used and these may be chosen from those mentioned within the textbooks referred to above. Particular $R_4$ groups that may be mentioned herein include, but are not limited to a tosyl group, a nosyl group, a diphenylphosphinyl group and suitable isomers thereof. As will be appreciated, the deprotected compound of formula I, where $R_4$ is H is also intended to form part of the current invention, as it involves the simple step of deprotecting the nitrogen group. This also applies for any other protecting groups on other substituents in the starting materials.

It will be noted that the $R_8$ group is also referred to herein as a protecting group. However, it is noted that the compound of formula IV is the catalytic species used in the reaction and it may be desired to retain this protecting group in situ once the reaction has been completed so that the catalyst may be reused without the need for the hydroxyl group to be re-protected. In general, any suitable groups that can be used to protect a hydroxyl group may be used as $R_8$. For example, $R_8$ may be an alkyl silane, such as trimethylsilane.

As will be appreciated, the compound of formula IV is intended to act as the catalyst for the reaction. Without wishing to be bound by theory, it is believed that the high enantio- and chemo-selectivities obtained herein are obtained through the use of this catalyst. In particular, it is believed that the enantioselectivity obtained in the method described herein is due to the use of an enantioenriched catalyst. When used herein, the enantioenriched catalyst may have an enantiomeric excess of greater than or equal to 90%, such as greater than or equal to 95%, such as greater than or equal to 98%. In particular embodiments of the invention that may be mentioned herein, the compound of formula IV may be:

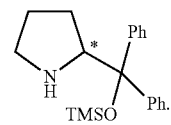

The use of the above compound may be more effective in providing high yields and enantioselectivities as compared to other known chiral amine catalysts. This is demonstrated in Example 1 (see Table 1, entry 1 vs 9-11).

While $KH_2PO_4$ may be used alone as the base in some embodiments of the invention, it is noted that an additional base may also be used in conjunction with this base. For example, the base may further comprise an additional base selected from one or more of the group consisting of $K_2HPO_4$, an amine base, and $Na_2HPO_4$. Any suitable amine base may be used in the reaction as the additional base. Examples of suitable amine bases include, but are not limited to $Et_3N$, 4-Dimethylaminopyridine (DMAP), and 1,4-diazabicyclo[2.2.2]octane (DABCO). In particular embodiments of the invention that may be mentioned herein the additional base may be $K_2HPO_4$.

While not necessary in order to obtain the desired product, it has been surprisingly found that the presence of an additive in the reaction mixture may help to suppress undesirable side-reactions and hence, maximise the yield of the desired product. This is demonstrated in Example 4. Any suitable additive capable of suppressing a side reaction may be used in the method disclosed herein. Examples of suitable additives include, but are not limited to LiBr, NaCl, KCl, and $MgCl_2$. In particular embodiments that may be mentioned herein, the additive may be NaCl.

Any suitable solvent may be used in the method described hereinbefore. For example, the solvent may consist essentially of an alkyl alcohol and water. Any suitable ratio of alkyl alcohol to water may be used in the solvent. For example, the alkyl alcohol:water volume:volume ratio may be from 90:10 to 99.5:0.5 or, more particularly, 99:1. In examples that may be mentioned herein, the solvent may be ethanol and water or, yet more particularly, methanol and water. For example, the solvent may be methanol and water in a 99:1 volume:volume ratio.

When used herein, the term "consists essentially of" is intended to mean that the solvent is formed from an alkyl alcohol and water, with the exception of possible contaminants in the solvent. As such, the total alkyl alcohol and water content of the solvent may be from 95 vol % to 100 vol % of the solvent, such as from 99 vol % to 100 vol % of the solvent, from 99.9 vol % to 100 vol % of the solvent.

The method described herein may be run at any suitable temperature, provided that it is sufficient to drive the reaction towards completion in a suitable period of time (e.g. less than 7 days). Examples of suitable temperatures for the reaction include, but are not limited to, a temperature of from 40 to 80° C. While the reaction may be conducted over an extended period of time, it may be conveniently completed within a relatively short time frame. Therefore, the reaction time may be from 1 hour to 48 hours, such as from 6 hours to 24 hours, such as about 12 hours. When used herein, "reaction time" refers to the time from the addition of the reactants together until the reaction is worked up. It will be appreciated that the reaction time may be extended beyond the upper limits listed here, though this may be detrimental in terms of consumption of power and other utilities (e.g. water), making the reaction uneconomical.

In embodiments of the invention, one or more of the following may apply:

(a) a molar ratio of the compound of formula III to the compound of formula II may be from 1.1:1 to 4:1;

(b) a molar ratio of $KH_2PO_4$ to the compound of formula II may be from 0.1:1 to 5:1, such as from 0.35:1 to 2:1 such as 1:1; and (c) a molar ratio of the catalyst of formula IV to the compound of formula II may be from 0.2:1 to 0.4:1.

In embodiments of the invention, one or more of the following may apply:

(a) a molar ratio of the compound of formula III to the compound of formula II may be 2:1'

(b) a molar ratio of $KH_2PO_4$ to the compound of formula II may be 1:1; and (c) a molar ratio of the catalyst of formula IV to the compound of formula I may be 0.3:1.

In embodiments of the invention where the method makes use of a further base in addition to $KH_2PO_4$, then a total molar ratio of the base comprising $KH_2PO_4$ and a further base relative to the compound of formula II may be from 1.5:1 to 2:1, where the $KH_2PO_4$ and the further base may have a molar ratio of 1:1.

In yet further embodiments of the invention a molar ratio of the additive to the compound of formula II may be about 1:1.

In an embodiment of the invention, the method involves reacting α,β-unsaturated imines and enals in the presence of a chiral amine to provide cyclic β-amino aldehydes with exceptional chemo- and stereoselectivities as described in Example 2. Key steps in this catalytic process involve 1,4-addition of the remote γ-carbon atoms of unsaturated imines to enals under the catalysis of chiral amines. As shown in Example 3, the amino aldehydes can be converted to cyclic β-amino acids bearing a quaternary stereocenter that is difficult to prepare using previous methods.

Further aspects and embodiments of the invention will now be discussed with respect to the following non-limiting examples.

EXAMPLES

The invention relates to a method of forming cyclic β-amino aldehydes by the direct nucleophilic addition of the remote γ-carbon atoms of α,β-unsaturated imines to enals under the catalysis of chiral secondary amine catalysts (FIG. 1(B)). Key steps include the reaction of enal (1) with amine catalyst to form unsaturated iminium intermediate I, and γ-CH deprotonation of unsaturated imine substrate (2) to form dienamine intermediate II. Addition of the γ-carbon atom of II to unsaturated iminium intermediate I affords intermediate III that can undergo further intramolecular Mannich reaction to form intermediate IV. Hydrolysis of the iminium component of intermediate IV leads to cyclic amino aldehyde product (3) with the regeneration of amine catalyst. In this cascade reaction, multiple atoms of both the enal and unsaturated imine substrates are involved with the formation of two new carbon-carbon bonds. The cyclic amino aldehyde products (3), obtained as essentially single enantiomers with up to 99% ee, can be readily transformed to cyclic β-amino acids after oxidations.

General Information

Commercially available materials purchased from Alfa Aesar or Aldrich were used as received. NMR spectra were recorded either on Bruker AV 300 (300 MHz), AVII 400 (400 MHz), or AV 500 (500 MHz) spectrometer. Chemical shifts were recorded in parts per million (ppm, δ) relative to tetramethylsilane (δ 0.00). $^1$H NMR splitting patterns were designated as singlet (s), doublet (d), triplet (t), quartet (q), dd (doublet of doublets); m (multiplets), and etc. All first-order splitting patterns were assigned on the basis of the appearance of the multiplet. Splitting patterns that could not be easily interpreted were designated as multiplet (m) or broad (br). IR spectra were collected on Shimadzu IRAffinity-1 spectrophotometer. High resolution mass spectral analysis (HRMS) was performed on Waters Q-TOF Premier mass spectrometer. The ee value was determined via HPLC analysis on stationary chiral phase using Shimadzu LC-20AD HPLC workstation. Optical rotations were measured using a 1 mL cell with a 1 cm path length on a Jasco P1030 digital polarimeter and are reported as follows: $[\alpha]_D^{20}$. Melting points were measured on OptiMelt Automated Melting Point system. Analytical thin-layer chromatography (TLC) was carried out on Merck 60 F254 pre-coated silica gel plate (0.2 mm thickness). Visualization was performed using a UV lamp. Good quality crystal of 3a (colorless block-like crystal) was obtained by vaporization of a $CH_2Cl_2$/petroleum ether solution of compound 3a. CCDC 1916911 contains the supplementary crystallographic data.

Preparation of Substrates

A: Preparation of α,β-Unsaturated Ketones

A1; Synthesis of P2a~P2d and P2h, the Precursors of α,β-unsaturated Imines 2a~2d, 2h~2k (*J. Chin. Chem. Soc.* 2004, 51, 581-583; *J. Am. Chem. Soc.* 2017, 139, 7737)

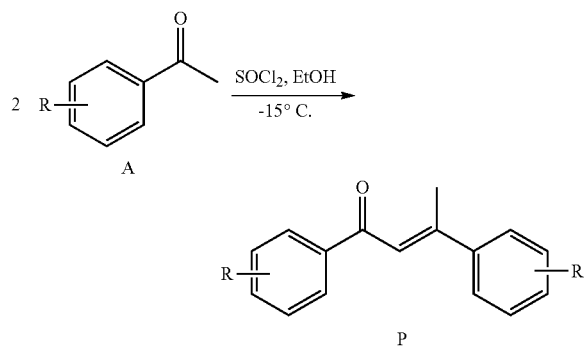

Example given for P2a (R=H). The solution of acetophenone (5.0 g, 28 mmol) in ethanol (11 ml) was cooled under −15° C. in a brine bath, followed by the addition of thionyl chloride (3.2 ml, 43 mmol) in 30 min through addition funnel. After addition, the reaction proceeded for additional 2 h under the same temperature, and was then quenched by addition of saturated $K_2CO_3$ solution in batches. The resulting solution was extracted with DCM (3×40 ml). The combined organic phase was washed with brine, dried (anhydrous $Na_2SO_4$), filtered, and concentrated under reduced pressure. The P2a was then obtained via column chromatography (Hexane/EtOAc 50:1) as yellow liquid (the P2a containing triarylbenzene can be used directly for the subsequent imine synthesis without further purification).

P2b~P2d and P2h were obtained using similar procedures.

A2: Synthesis of P2e and P2f, the Precursors of α,β-unsaturated Imine 2e and 2f (*J. Am. Chem. Soc.* 2011, 133, 8432)

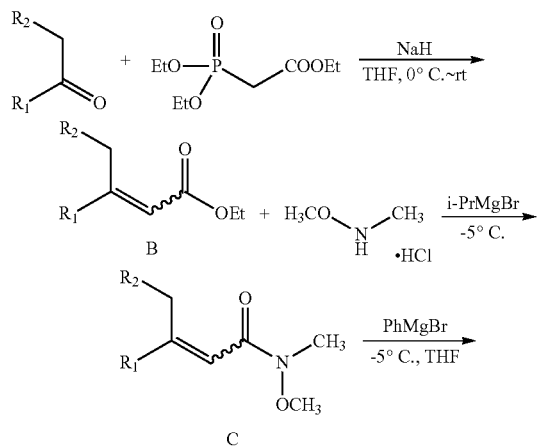

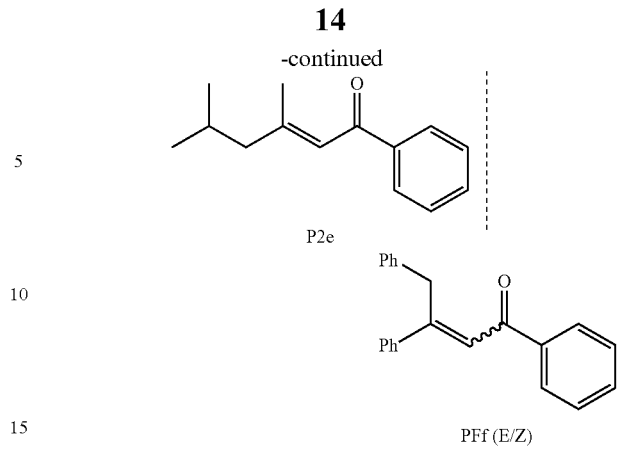

To a suspension of NaH (60% dispersion in oil, 20 mmol) in THF (10 mL) was added a solution of triethyl phosphonoacetate (26 mmol) in THF (10 mL) under an nitrogen atmosphere at 0° C. After being stirred at room temperature for 30 min, a THF solution of corresponding ketones (20 mmol) was added to the reaction mixture at 0° C. After being further stirred at room temperature for 24 h, the reaction was quenched by adding sat. aq. $NaHCO_3$ (30 mL) and extracted with EtOAc. The organic layer was separated and washed with brine, dried over anhydrous $Na_2SO_4$ and concentrated at reduced pressure. The residue was purified by silica gel column chromatography (Hexane/EtOAc 20:1) to get the isomer mixtures of B (E/Z isomer mixture).

To a suspension of α,β-unsaturated ester B (10 mmol) obtained above and N,O-dimethylhydroxylamine hydrochloride (2 eq) in THF (15 mL) was added dropwise i-PrMgCl (2.0 M solution in THF, 10 mL) under nitrogen atmosphere at −5° C. After being stirring at same temperature, the reaction was quenched by addition of sat. aq. $NH_4Cl$ and extracted with EtOAc. The organic layer was separated and washed with brine, dried over $Na_2SO_4$ and concentrated at reduced pressure to afford the residue containing E and Z isomer (for P2e, the corresponding E Weinreb amide could be obtained for next step by silica gel column chromatography eluted with Hexane/DCM/EtOAc 3:0.8:0.2).

To a solution of the Weinreb amide C (6 mmol) obtained above in THF (2.0 mL) was added dropwise a solution of the Phenylmagnesium Bromide (1.5 eq) under nitrogen atmosphere at −5° C. After being stirring at 0° C. for 30 min, the reaction was quenched by adding sat. aq. $NH_4Cl$ and extracted with EtOAc. The organic layer was separated and washed with brine, dried over $Na_2SO_4$ and concentrated at reduced pressure. The residue was purified by silica gel column chromatography (Hexane/EtOAc 10:1) to afford α,β-unsaturated ketone P2e and P2f.

A3: Synthesis of P2g, the Precursors of α,β-unsaturated Imine 2g (*Adv. Synth. Catal.* 2014, 356, 2787)

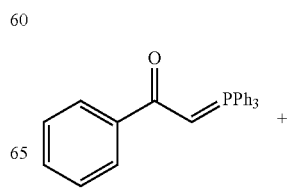

-continued

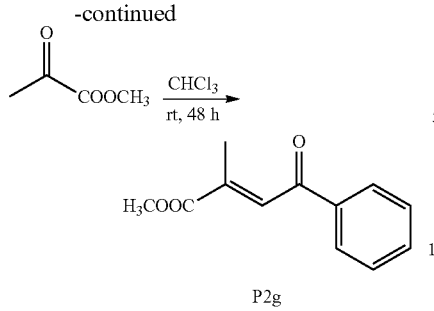

P2g

1-Phenyl-2-(triphenylphosphoranylidene)ethanone (17 mmol) and methyl 2-oxopropanoate (15 mmol) were dissolved in CHCl$_3$ at rt, and stirred for 48 h. The resulting solution was concentrated and directly subjected to silica gel column chromatography (Hexane/EtOAc 15:1) to afford the desired product P2g.

B: Preparation of α,β-Unsaturated Imines

B1: Synthesis of Imines 2a~2i and 2k (*Org. Lett.* 2012, 14, 2382)

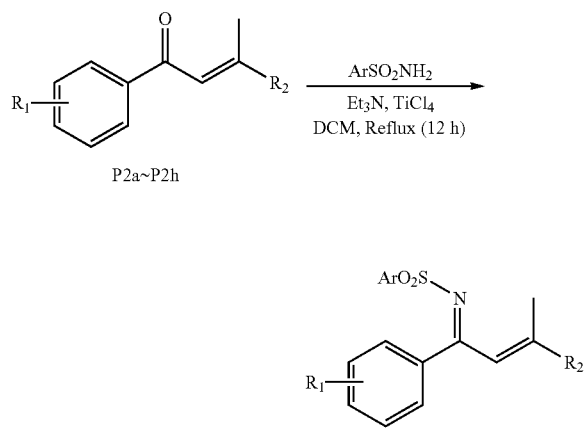

2a~2i, 2k

To a mixture of P2a (5 mmol), arylsulfonamide (1.2 eq), and Et$_3$N (2.5 eq) in DCM (20 mL) at 0° C., was slowly added 1.0 M solution of TiCl$_4$ in DCM (7.5 mL, 1.5 eq). The reaction mixture was initially stirred at 0° C. for 0.5 h, and then refluxed for 12 h. After complete consumption of P2a (monitored by TLC), the reaction mixture was diluted with H$_2$O, and the organic layer was separated. The aqueous layer was extracted with DCM and the combined organic layer was washed water and dried over anhydrous Na$_2$SO$_4$. After removal of the organic solvent under vacuum, the residue was purified by silica gel column chromatography (Hexane/DCM/EtOAc 3:1.5:0.1) to get viscous solid, which was recrystallized using Hexane/EtOAc as solvent to get pure 2a.

2b~2i and 2k were obtained using similar procedures.

B2: Synthesis of Imine 2 (*J. Am. Chem. Soc.* 2008, 130, 6918; *Angew. Chem. Int. Ed.* 2014, 53, 3462; *Angew. Chem.* 2014, 126, 3530)

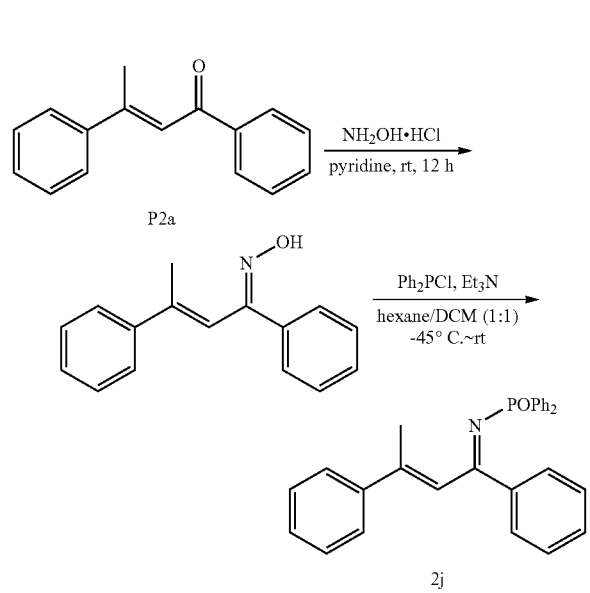

P2a (2.25 g, 10 mmol) and hydroxylamine hydrochloride (0.83 g, 1.2 eq) with pyridine (1.8 mL, 2.2 eq) were reacted in methanol (20 mL) at room temperature for 20 h. After removal of the organic solvent under vacuum, the residue was purified by flash chromatography (Hexane/EtOAc 7:1) to afford the corresponding oxime as an off-white solid.

To a solution of oxime (0.71 g, 3 mmol) in DCM/n-Hexane (1:1, 10 ml) under N$_2$ atmosphere at −45° C. was added triethylamine (1.1 eq) and stirred for 10 min. Subsequently, chlorodiphenylphosphine (1.1 eq) was added dropwise over 20 min. After stirring at −45° C. for 1 h and at rt for 16 h, the solvents were removed under reduced pressure (temperature of water bath at 20° C.). The crude reaction mixture was dissolved in DCM and washed with H$_2$O. The organic phase was dried over Na$_2$SO$_4$, filtered and concentrated. The residue was purified by flash column chromatography (Hexane/EtOAc 2:1) to obtain desired α,β-unsaturated imine 2j.

B3: Synthesis of imine 2l (*Tetrahedron Lett.* 1988, 29, 3752)

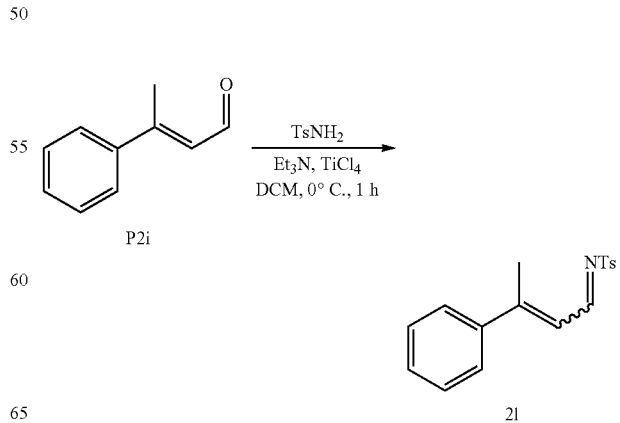

To a mixture of P2i (5 mmol), p-toluenesulfonamide (1.2 eq), and Et$_3$N (2.5 eq) in DCM (10 mL) at 0° C., was slowly added 1.0 M solution of TiCl$_4$ in DCM (7.5 mL, 1.5 eq). After the addition was complete, the resulting mixture was stirred for 1 h at the same temperature. After complete consumption of P2i (monitored by TLC), the reaction mixture was diluted with H$_2$O, and the organic layer was separated. The aqueous layer was extracted with DCM and the combined organic layer was washed water and dried over anhydrous Na$_2$SO$_4$. After removal of the organic solvent under vacuum, the residue was purified by silica gel column chromatography (Hexane/EtOAc 10:1) to get 2l as yellow liquid containing E/Z isomers (E:Z 2.3:1).

C: Characterization of Substrates 2a~2l

N-((1Z,2E)-1,3-diphenylbut-2-en-1-ylidene)-4-methylbenzenesulfonamide (2a)

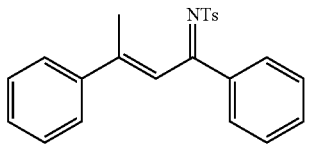

Light yellow solid, m.p. 122~124° C.;
$^1$H NMR (500 MHz, CDCl$_3$) δ 7.93 (d, J=7.8 Hz, 2H), 7.89 (d, J=8.3 Hz, 2H), 7.58 (d, J=7.3 Hz, 2H), 7.57-7.53 (m, 1H), 7.46-7.38 (m, 4H), 2a 7.40-7.35 (m, 1H), 7.28 (d, J=8.0 Hz, 2H), 7.06 (s, 1H), 2.42 (s, 3H), 1.79 (s, 3H);
$^{13}$C NMR (101 MHz, CDCl$_3$) δ 178.46, 145.34, 143.59, 140.86, 138.42, 137.10, 133.56, 129.90, 129.50, 128.95, 128.90, 128.70, 127.55, 126.34, 121.85, 21.71, 19.41;
HRMS (ESI) m/z 376.1368 [M+H]$^+$ (calcd for C$_{23}$H$_{22}$NO$_2$S 376.1371, err −0.8 ppm);
IR v$_{max}$: 1632, 1597, 1582, 1543, 1445, 1315, 1298, 1271, 1146, 1092, 827, 812, 764, 754, 689 cm$^{-1}$.

N-((1Z,2E)-1,3-bis(4-fluorophenyl)but-2-en-1-ylidene)-4-methylbenzenesulfonamide (2b)

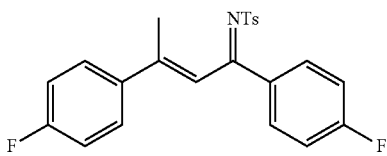

Colorless transparent solid, m.p. 81~82° C.;
$^1$H NMR (400 MHz, CDCl$_3$) δ 7.95 (dd, J=8.7, 5.7 Hz, 2H), 7.88 (d, J=8.3 Hz, 2H), 7.56 (dd, J=8.8, 5.3 Hz, 2H), 7.30 (d, J=8.0 Hz, 2H), 7.10 (td, J=8.7, 2.2 Hz, 4H), 6.97 (s, 1H), 2.43 (s, 3H), 1.80 (s, 3H);
$^{19}$F NMR (282 MHz, CDCl$_3$) δ −104.21, −112.67;
$^{13}$C NMR (101 MHz, CDCl$_3$) δ 176.65, 166.32 (d, J=256.5 Hz), 163.29 (d, J=248.9 Hz), 143.96, 143.74, 138.39, 136.88, 133.15, 132.42 (d, J=9.3 Hz), 129.56, 128.17 (d, J=8.2 Hz), 127.52, 121.57, 116.22 (d, J=22.1 Hz), 115.67 (d, J=21.6 Hz), 21.70, 19.45;

HRMS (ESI) m/z 412.1181 [M+H]$^+$ (calcd for C$_{23}$H$_{20}$NO$_2$SF$_2$ 412.1183, err −0.5 ppm);
IR v$_{max}$: 1634, 1599, 1568, 1506, 1406, 1308, 1229, 1146, 1086, 818, 768, 667, 596, 552, 536 cm$^{-1}$.

N-((1Z,2E)-1,3-bis(4-bromophenyl)but-2-en-1-ylidene)-4-methylbenzenesulfonamide (2c)

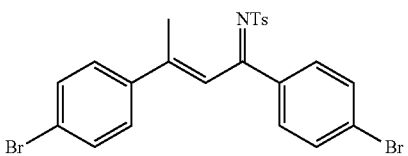

Yellowish white powder, m.p. 115~117° C.;
$^1$H NMR (400 MHz, CDCl$_3$) δ 7.88 (d, J=8.4 Hz, 2H), 7.77 (d, J=8.2 Hz, 2H), 7.61-7.50 (m, 4H), 7.44 (d, J=8.7 Hz, 2H), 7.30 Br B (d, J=8.0 Hz, 2H), 7.00 (s, 1H), 2.43 (s, 3H), 1.79 (s, 3H);
$^{13}$C NMR (101 MHz, CDCl$_3$) δ 176.70, 144.07, 143.88, 139.63, 138.18, 135.71, 132.34, 131.91, 131.21, 129.61, 129.03, 127.96, 127.56, 123.28, 121.87, 21.73, 19.30;
HRMS (ESI) m/z 531.9575 [M+H]$^+$ (calcd for C$_{23}$H$_{20}$NO$_2$SBr$_2$ 531.9581, err −1.1 ppm);
IR v$_{max}$: 1638, 1594, 1578, 1543, 1481, 1402, 1317, 1152, 1094, 1072, 1005, 833, 799, 787, 762, 714, 699, 551, 536 cm$^{-1}$.

N-((1Z,2E)-1,3-di(naphthalen-2-yl)but-2-en-1-ylidene)-4-methylbenzenesulfonamide (2d)

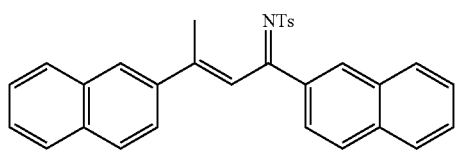

Yellowish powder, m.p. 120~121° C.;
$^1$H NMR (400 MHz, CDCl$_3$) δ 8.44 (d, J=1.8 Hz, 1H), 8.07 (dd, J=8.6, 1.9 Hz, 1H), 8.02 (d, J=1.8 Hz, 1H), 7.98-7.83 (m, 8H), 7.80 (dd, J=8.6, 1.9 Hz, 1H), 7.59 (ddd, J=8.2, 6.8, 1.3 Hz, 1H), 7.54-7.49 (m, 3H), 7.32-7.25 (m, 3H), 2.40 (s, 3H), 1.90 (s, 3H);
$^{13}$C NMR (101 MHz, CDCl$_3$) δ 178.41, 144.72, 143.60, 138.51, 137.97, 135.97, 134.51, 133.59, 133.38, 132.85, 132.63, 129.76, 129.53, 128.93, 128.83, 128.64, 128.43, 127.93, 127.77, 127.67, 127.00, 126.75, 126.64, 125.75, 124.87, 124.10, 122.46, 21.69, 19.35;
HRMS (ESI) m/z 476.1677 [M+H]$^+$ (calcd for C$_{31}$H$_{26}$NO$_2$S 476.1684, err −1.5 ppm);
IR v$_{max}$: 1638, 1614, 1597, 1576, 1539, 1504, 1435, 1313, 1302, 1285, 1227, 1196, 1153, 1090, 949, 814, 750, 667, 571 cm$^{-1}$.

N-((1Z,2E)-3,5-dimethyl-1-phenylhex-2-en-1-ylidene)-4-methylbenzenesulfonamide (2e)

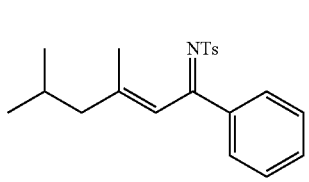

Yellowish white powder, m.p. 89~91° C.;

$^1$H NMR (300 MHz, CDCl$_3$) δ 7.90 (d, J=8.2 Hz, 2H), 7.81 (d, J=7.4 Hz, 2H), 7.51 (t, J=7.4 Hz, 1H), 7.39 (t, J=7.7 Hz, 2H), 7.31 (d, J=8.0 Hz, 2H), 6.61 (s, 1H), 2.42 (s, 3H), 2.13 (d, J=7.5 Hz, 2H), 1.93 (dp, J=13.5, 6.7 Hz, 1H), 1.41 (3H, s), 1.01 (d, J=6.5 Hz, 6H);

$^{13}$C NMR (75 MHz, CDCl$_3$) δ 178.59, 150.48, 143.33, 138.96, 137.93, 133.01, 129.74, 129.42, 128.72, 127.35, 121.52, 49.73, 26.85, 22.80, 21.68, 20.40;

HRMS (ESI) m/z 356.1678 [M+H]$^+$ (calcd for C$_{21}$H$_{26}$NO$_2$S 356.1684, err −1.7 ppm);

IR ν$_{max}$: 2951, 2924, 2828, 1647, 1597, 1582, 1555, 1450, 1313, 1288, 1180, 1155, 1090, 860, 824, 802, 775, 747, 688, 569, 540 cm$^{-1}$.

4-Methyl-N-((1Z,3Z)-1,3,4-triphenylbuta-1,3-dien-1-yl)benzenesulfonamide (2f)

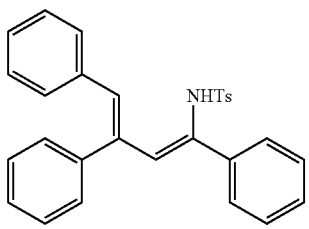

Colorless solid, m.p. 139~141° C.;

$^1$H NMR (400 MHz, CDCl$_3$) δ 7.52-7.45 (m, 2H), 7.40-7.35 (m, 6H), 7.34-7.29 (m, 5H), 7.27-7.18 (m, 4H), 7.07 (d, J=8.0 Hz, 2H), 6.66 (s, 1H), 6.21 (s, 1H), 5.96 (s, 1H), 2.24 (s, 3H);

$^{13}$C NMR (101 MHz, CDCl$_3$) δ 143.86, 140.63, 137.53, 136.94, 136.86, 136.66, 135.55, 131.89, 129.50, 129.48, 129.24, 128.89, 128.62, 128.51, 128.23, 128.09, 127.85, 127.58, 127.21, 119.92, 21.58;

HRMS (ESI) m/z 452.1677 [M+H]$^+$ (calcd for C$_{29}$H$_{26}$NO$_2$S 452.1684, err −1.5 ppm);

IR ν$_{max}$: 3292, 1620, 1595, 1490, 1446, 1383, 1325, 1165, 1009, 926, 816, 787, 754, 698, 658, 583, 546, 532 cm$^{-1}$.

Methyl (2E,4Z)-2-methyl-4-phenyl-4-(tosylimino)but-2-enoate (2q)

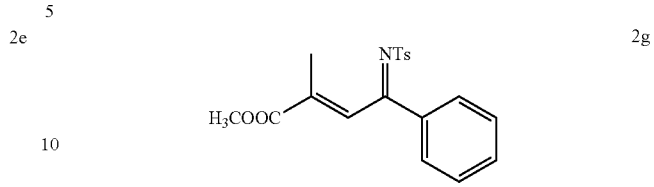

Yellow liquid;

$^1$H NMR (500 MHz, CDCl$_3$) δ 7.90 (d, J=8.4 Hz, 2H), 7.88 (d, J=7.7 Hz, 2H), 7.67 (d, J=1.5 Hz, 1H), 7.57 (t, J=7.4 Hz, 1H), 7.42 (dd, J=8.4, 7.4 Hz, 2H), 7.34 (d, J=7.9 Hz, 2H), 3.86 (s, 3H), 2.44 (s, 3H), 1.69 (d, J=1.3 Hz, 3H);

$^{13}$C NMR (101 MHz, CDCl$_3$) δ 175.49, 166.62, 144.05, 137.61, 134.85, 134.22, 133.53, 129.58, 129.03, 127.63, 52.63, 21.67, 15.54;

HRMS (ESI) m/z 358.1104 [M+H]$^+$ (calcd for C$_{19}$H$_{20}$NO$_4$S 358.1113, err −2.5 ppm);

IR ν$_{max}$: 1724, 1717, 1664, 1585, 1558, 1435, 1321, 1269, 1254, 1157, 1123, 1094, 806, 752, 739, 687, 677, 546 cm$^{-1}$.

N-((1Z,2E)-1,3-diphenylbut-2-en-1-ylidene)-2-nitrobenzenesulfonamide (2h)

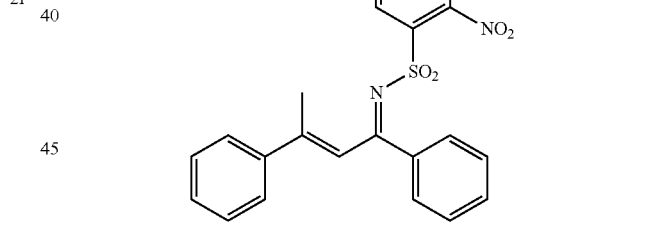

Yellow solid, m.p. 150~152° C.;

$^1$H NMR (400 MHz, CDCl$_3$) δ 8.28 (d, J=9.3 Hz, 1H), 7.95 (d, J=7.3 Hz, 2H), 7.84 (d, J=9.3 Hz, 1H), 7.75-7.67 (m, 2H), 7.61-7.54 (m, 3H), 7.45 (t, J=7.8 Hz, 2H), 7.43-7.37 (m, 3H), 7.03 (s, 1H), 1.93 (s, 3H);

$^{13}$C NMR (101 MHz, CDCl$_3$) δ 179.04, 148.06, 140.72, 136.76, 135.01, 133.89, 133.63, 132.52, 130.28, 130.14, 129.15, 129.03, 128.71, 126.38, 124.83, 121.93, 19.58;

HRMS (ESI) m/z 407.1065 [M+H]$^+$ (calcd for C$_{22}$H$_{19}$N$_2$O$_4$S 407.1066, err −0.2 ppm);

IR ν$_{max}$: 1618, 1582, 1547, 1530, 1443, 1364, 1312, 1294, 1277, 1148, 1120, 1060, 866, 851, 829, 799, 783, 762, 745, 725, 692, 665, 640, 594, 542, 492 cm$^{-1}$.

N-((1Z,2E)-1,3-diphenylbut-2-en-1-ylidene)-4-nitrobenzenesulfonamide (2i)

Yellowish powder, m.p. 157~159° C.;

$^1$H NMR (400 MHz, CDCl$_3$) δ 8.36 (d, J=8.5 Hz, 2H), 8.22 (d, J=8.7 Hz, 2H), 7.92 (d, J=7.7 Hz, 2H), 7.71-7.54 (m, 3H), 7.50-7.37 (m, 5H), 7.10 (s, 1H), 1.90 (s, 3H);

$^{13}$C NMR (101 MHz, CDCl$_3$) δ 179.98, 150.14, 147.12, 140.67, 136.69, 134.14, 130.02, 129.31, 129.10, 128.83, 128.68, 126.37, 124.18, 121.60, 19.68;

HRMS (ESI) m/z 407.1066 [M+H]$^+$ (calcd for C$_{22}$H$_{19}$N$_2$O$_4$S 407.1066, err 0 ppm);

IR ν$_{max}$: 1607, 1578, 1545, 1531, 1514, 1443, 1350, 1312, 1275, 1175, 1152, 1096, 1084, 1011, 858, 824, 760, 746, 737, 692, 662, 586, 542, 536 cm$^{-1}$.

N-((1Z,2E)-1,3-diphenylbut-2-en-1-ylidene)-P,P-diphenylphosphinic amide (2j)

Yellow liquid;

$^1$H NMR (300 MHz, CDCl$_3$) δ 8.07 (d, J=7.0 Hz, 2H), 8.06-7.92 (m, 4H), 7.60-7.53 (m, 3H), 7.52-7.32 (m, 11H), 7.10 (q, J=1.2 Hz, 1H), 1.59 (d, J=1.1 Hz, 3H);

$^{31}$P NMR (121 MHz, CDCl$_3$) δ 19.87;

$^{13}$C NMR (75 MHz, CDCl$_3$) δ 181.64 (d, J=8.0 Hz), 142.30, 141.34, 139.28 (d, J=23.5 Hz), 134.71 (d, J=128.4 Hz), 132.63, 131.69 (d, J=9.1 Hz), 131.31 (d, J=2.8 Hz), 129.29, 128.70, 128.46, 128.33 (d, J=12.4 Hz), 128.28, 126.26, 125.28 (d, J=13.3 Hz), 18.80;

HRMS (ESI) m/z 422.1670 [M+H]$^+$ (calcd for C$_{23}$H$_{25}$NOP 422.1674, err −0.9 ppm); IR ν$_{max}$: 1614, 1587, 1554, 1437, 1312, 1269, 1200, 1121, 1107, 829, 752, 725, 691, 546, 529 cm$^{-1}$.

N-((1Z,2E)-1,3-di-p-tolylbut-2-en-1-ylidene)-4-methylbenzenesulfonamide (2k)

White solid, m.p. 101~103° C.;

$^1$H NMR (400 MHz, CDCl$_3$) δ 7.87 (d, J=8.3 Hz, 2H), 7.82 (d, J=8.0 Hz, 2H), 7.47 (d, J=8.2 Hz, 2H), 7.30-7.24 (m, 2H), 7.212 (d, J=8.1 Hz, 2H), 7.207 (d, J=8.3 Hz, 2H), 7.00 (s, 1H), 2.44-2.36 (m, 9H), 1.73 (s, 3H);

$^{13}$C NMR (101 MHz, CDCl$_3$) δ 178.61, 144.89, 144.62, 143.37, 138.93, 138.68, 138.02, 134.57, 130.05, 129.64, 129.42, 129.36, 127.56, 126.22, 121.24, 21.82, 21.67, 21.32, 19.27;

HRMS (ESI) m/z 404.1682 [M+H]$^+$ (calcd for C$_{25}$H$_{26}$NO$_2$S 404.1684, err −0.5 ppm); IR ν$_{max}$: 1626, 1605, 1574, 1539, 1319, 1298, 1283, 1179, 1153, 1094, 1018, 839, 799, 775, 766, 667, 594, 565, 530 cm$^{-1}$.

4-Methyl-N-(3-phenylbut-2-en-1-ylidene)benzenesulfonamide (2l)

Yellowish liquid;

$^1$H NMR (400 MHz, CDCl$_3$) for E isomer δ 9.19 (d, J=10.0 Hz, 1H), 7.89 (d, J=8.3 Hz, 2H), 7.60-7.54 (m, 2H), 7.48-7.39 (m, 2H), 7.36 (d, J=7.8 Hz, 2H), 7.26-7.22 (m, 1H), 6.77 (dq, J=10.1, 1.3 Hz, 1H), 2.54 (d, J=1.2 Hz, 3H), 2.46 (s, 3H);

$^{13}$C NMR (101 MHz, CDCl$_3$) for E isomer δ 166.99, 160.45, 144.38, 140.20, 135.59, 130.49, 129.77, 128.82, 127.92, 126.43, 123.58, 21.65, 17.32;

HRMS (ESI) m/z 300.1057 [M+H]$^+$ (calcd for C$_{17}$H$_{18}$NO$_2$S 300.1058, err −0.3 ppm); IR ν$_{max}$: 1653, 1609, 1574, 1447, 1364, 1317, 1256, 1184, 1152, 1086, 883, 824, 810, 760, 737, 729, 681, 586, 550 cm$^{-1}$.

General Procedure 1

-continued

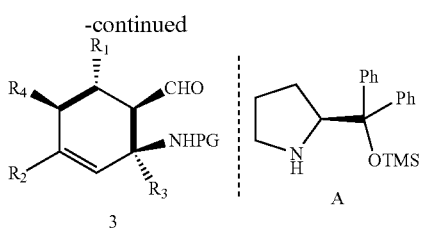

The following process is intended as a general guide to the reaction conditions that may be used in this reaction. These conditions may be varied by a skilled person in accordance with the deviations set out below. For example, the amount of base (and composition thereof), amount of additive, solvent composition, time, and temperature may all be varied.

Thus, unless otherwise specified, to a dry Schlenk tube equipped with a magnetic stir bar, was added aldehyde 1 (0.4 mmol), imine 2 (0.2 mmol), diphenylprolinol silyl ether A (0.06 mmol), $K_2HPO_4$ (0.2 mmol), $KH_2PO_4$ (0.2 mmol), and NaCl (0.2 mmol). The tube was closed with a septum, evacuated, and refilled with nitrogen. Unless otherwise specified, MeOH/$H_2O$ (99:1, 2 mL) was then added. Unless otherwise specified, the reaction mixture was stirred at 60° C. for 12 h. The mixture was concentrated under reduced pressure. Unless otherwise specified, the resulting crude residue was purified via column chromatography on silica gel (Hexane/DCM/EtOAc 3:0.8:0.2) to afford the desired product 3.

Note: Racemic samples for HPLC analysis on chiral stationary phase were prepared using (R) and (S) mixture (1:1) of diphenylprolinol silyl ether A. Absolute configuration of the product was assigned based on X-ray structure of 3a.

Example 1: Optimization of Reaction Conditions for the Synthesis of 3a

Compound 3a was prepared from substrates enal 1a and α,β-unsaturated imine 2a following General Procedure 1 using the reaction conditions listed in Table 1.

TABLE 1

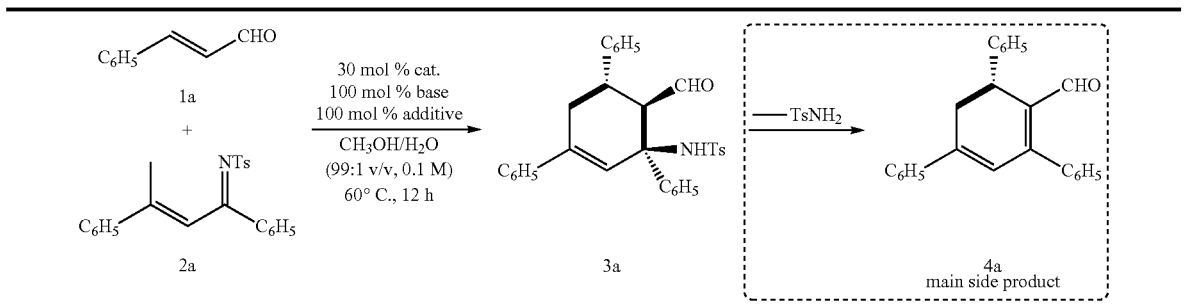

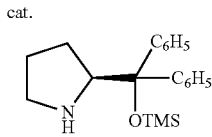

A

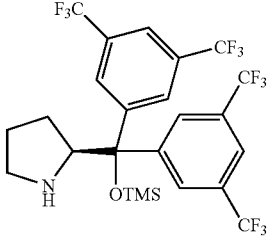

B

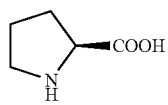

C

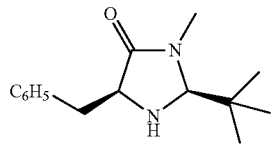

D

| Entry | Catalyst | Base | Additive | Yield [%] 3a[c]/4a[d] | Ee[e] 3a/4a |
|---|---|---|---|---|---|

TABLE 1-continued

| | | | | | |
|---|---|---|---|---|---|
| 1 | A | KH$_2$PO$_4$ | — | 64/6 | 99/93 |
| 2 | A | K$_2$HPO$_4$ | — | trace/— | —/— |
| 3 | A | K$_2$HPO$_4$, KH$_2$PO$_4$[b] | — | 23/10 | 99/94 |
| 4 | A | K$_3$PO$_4$, KH$_2$PO$_4$[b] | — | trace/— | —/— |
| 5 | A | K$_2$CO$_3$, KH$_2$PO$_4$[b] | — | trace/— | —/— |
| 6 | A | KH$_2$PO$_4$ | NaCl | 56/— | 99/— |
| 7 | A | K$_2$HPO$_4$, KH$_2$PO$_4$[b] | NaCl | 72 (69)[d]/4 | 99/93 |
| 8 | A | K$_2$HPO$_4$, KH$_2$PO$_4$[b] | LiBr | 55/7 | 99/86 |
| 9 | B | As entry 7 | | trace/— | —/— |
| 10 | C | As entry 7 | | 20/— | 29/— |
| 11 | D | As entry 7 | | 0/— | —/— |
| 12 | A | Et$_3$N/KH$_2$PO$_4$ | — | 55/— | 99/— |
| 13 | A | DMAP/KH$_2$PO$_4$ | — | 34/— | 99/— |
| 14 | A | DABCO/KH$_2$PO$_4$ | — | 64/— | 99/— |
| 15 | A | NaOAc/KH$_2$PO$_4$ | — | 50/— | 99/— |
| 16 | A | KH$_2$PO$_4$/Na$_2$HPO$_4$·2H$_2$O | — | 66/— | 99/— |
| 17 | A | K$_2$HPO$_4$, KH$_2$PO$_4$[b] | LiF | 33/— | 87/— |
| 19 | A | K$_2$HPO$_4$, KH$_2$PO$_4$[b] | KCl | 53/— | 99/— |
| 20 | A | K$_2$HPO$_4$, KH$_2$PO$_4$[b] | NaBF$_4$ | 37/— | 90/— |
| 21 | A | K$_2$HPO$_4$, KH$_2$PO$_4$[b] | MgCl$_2$ | 62/— | 99/— |
| 22 | A | KH$_2$PO$_4$ | NaCl | 56/— | 99/— |
| 23 | A | DABCO/KH$_2$PO$_4$ | NaCl | 66/— | 99/— |
| 24 | A | KH$_2$PO$_4$/Na$_2$HPO$_4$·2H$_2$O | KCl | 63/— | 99/— |

[a]Reaction conditions: 1a (0.2 mmol), 2a (0.1 mmol), amine (0.03 mmol), base (0.1 mmol), additive (0.1 mmol) in 1 mL CH$_3$OH/H$_2$O (99:1) at 60° C. for 12 h.
[b]100 mol % of each base was used.
[c]NMR yield based on 2a using trimethoxylbenzene as internal standard.
[d]Data in parenthesis indicated isolated yield of 3a.
[e]Enantiomeric excess of 3a was determined via HPLC analysis on chiral stationary phase.

Discussion

It was found that with the use of a chiral secondary amine, the Hayashi-Jorgensen type prolinol TMS ether (*Angew. Chem.* 2005, 117, 4284-4287; *Angew. Chem. Int. Ed.* 2005, 44, 4212-4215) as the amine catalyst, KH$_2$PO$_4$ as the base, the proposed cyclic amino aldehyde product (3a) could be obtained as essentially a single enantiomer with 64% yield and 99% ee (entry 1).

A mixture of CH$_3$OH with water (99:1 v/v) was found as an optimal solvent. Less than 13% yield or trace product was observed when the following solvents were used: ethyl acetate (EtOAc), dichloromethane (DCM), toluene, anhydrous methanol and tetrahydrofuran (THF).

Trace product was observed when KH$_2$PO$_4$ was replaced with K$_2$HPO$_4$ (entry 2). Dual basic additives (such as K$_3$PO$_4$/KH$_2$PO$_4$ and K$_2$CO$_3$/KH$_2$PO$_4$) were then explored for further optimization. The dual basic additives tested gave optically pure product 3a (99% ee) in low yields (trace to 23%, entries 3-5). Through the addition of NaCl as a salt additive, the yield of 3a dropped to 56% when KH$_2$PO$_4$ alone was used as the base (entry 6). However, the yield of the product 3a could be dramatically increased by the addition of NaCl with K$_2$HPO$_4$/KH$_2$PO$_4$ as the bases (entries 7 vs 3). Other inorganic salts (e.g. entries 8 and 17-24) were also tested as additives for this reaction.

Adduct 4a was obtained as the major side product, and its formation was suppressed by the addition of NaCl (entries 7 vs 3; see also Example 4 for discussion). Several other amine catalysts (B, C and D) tested were not effective (entries 9-11).

Example 2: Synthesis of 3a~3s

Compounds 3a~3s were prepared following General Procedure 1 above with appropriate variations in said procedure where necessary/desired. The compounds made, and their starting materials, are outlined in Table 2 below and FIG. 2.

TABLE 2

| Enal (1) | Imine (2) | Compound 3a~3s |
|---|---|---|
| (structure of 1a: cinnamaldehyde, PhCH=CHCHO) | (structure of 2a: N-tosyl imine with methyl and styryl groups on carbon, phenyl on nitrogen-bearing carbon) | (structure of 3a: cyclohexene bearing Ph, CHO, Ph, NHTs substituents with defined stereochemistry) |

TABLE 2-continued

| Enal (1) | Imine (2) | Compound 3a~3s |
|---|---|---|
| 4-methylcinnamaldehyde | 2a | 3b |
| 4-methoxycinnamaldehyde | 2a | 3c |
| 4-chlorocinnamaldehyde | 2a | 3d |
| 4-bromocinnamaldehyde | 2a | 3e |

TABLE 2-continued

| Enal (1) | Imine (2) | Compound 3a~3s |
|---|---|---|
| (2-methylcinnamaldehyde) | 2a | 3f |
| (furan-2-yl acrolein) | 2a | 3g |
| (2-naphthyl acrolein) | 2a | 3h |
| (cinnamylideneacetaldehyde) | 2a | 3i |
| (crotonaldehyde) | 2a | 3j |

TABLE 2-continued
| Enal (1) | Imine (2) | Compound 3a~3s |
|---|---|---|
| 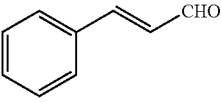 1a | 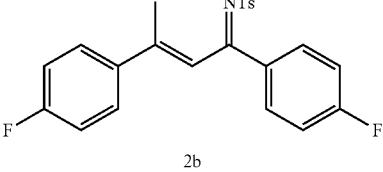 2b | 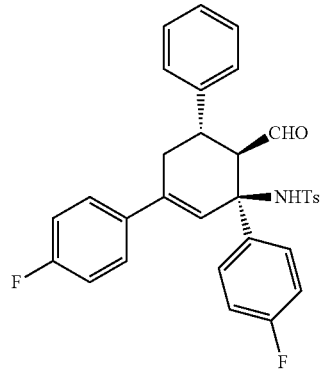 3k |
| 1a |  2c | 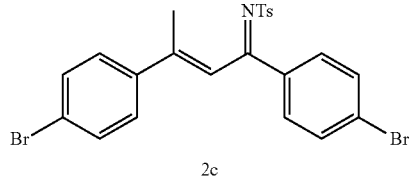 3l |
| 1a | 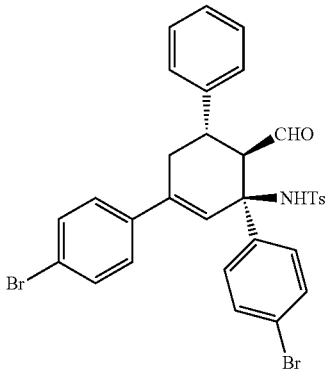 2d |  3m |
| 1a | 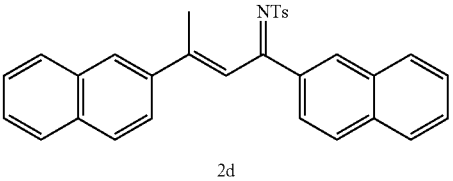 2e | 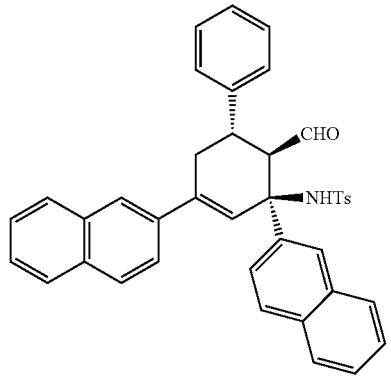 3n |

TABLE 2-continued
| Enal (1) | Imine (2) | Compound 3a~3s |
|---|---|---|
| 1a | 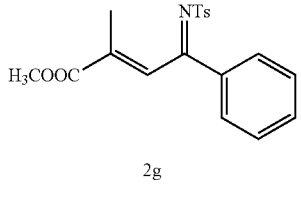<br>2g | 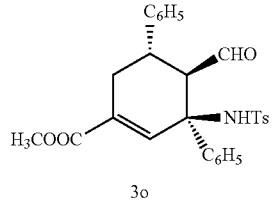<br>3o |
| 1a | 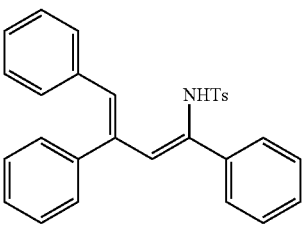<br>2f | 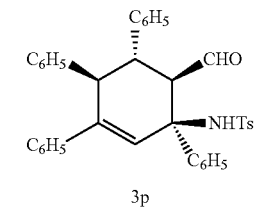<br>3p |
| 1a | 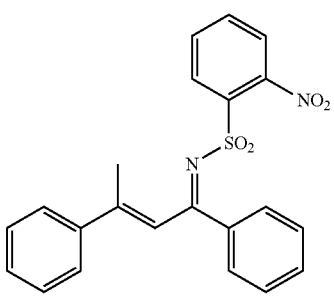<br>2h | 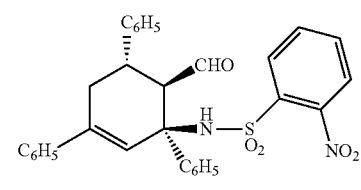<br>3q |
| 1a | 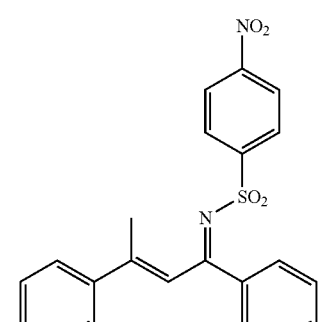<br>2i | 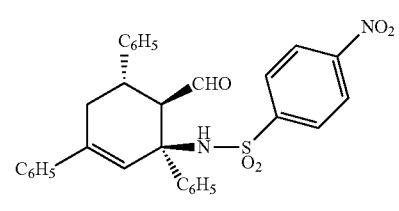<br>3r |
| 1a | 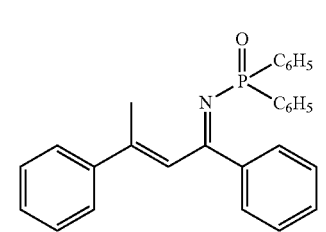<br>2j | 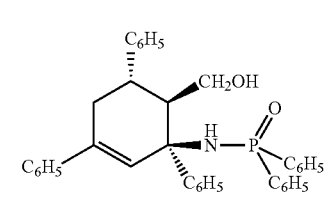<br>3s |

Characterization of Compounds 3a~3s and Side-Products 4a, 4e and 4g

N-((1'S,2'R,3'S)-2'-formyl-5'-phenyl-3',4'-dihydro-[1,1':3',1''-terphenyl]-1'(2'H)-yl)-4-methylbenzenesulfonamide (3a)

Colorless solid, m.p. 92~94° C., yield: 70 mg (69%); $[\alpha]^{20}_D$=−43.8 (c 1.06, CHCl$_3$);
$^1$H NMR (400 MHz, CDCl$_3$) δ 9.19 (d, J=1.6 Hz, 1H), 7.67 (d, J=8.0 Hz, 2H), 7.55 (d, J=7.6 Hz, 2H), 7.41-7.15 (m, 13H), 7.04 (d, J=8.0 Hz, 2H), 6.86 (s, 1H), 6.36 (br. s, 1H), 3.44 (dd, J=12.0, 1.6 Hz, 1H), 3.27 (td, J=11.3, 5.7 Hz, 1H), 2.61 (ddd, J=18.2, 10.8, 2.2 Hz, 1H), 2.39 (ddd, J=18.2, 5.8, 1.6 Hz, 1H), 2.30 (s, 3H);
$^{13}$C NMR (101 MHz, CDCl$_3$) δ 206.83, 144.49, 142.65, 140.77, 140.14, 139.06, 139.00, 129.25, 129.20, 128.67, 128.41, 128.31, 127.69, 127.65, 127.59, 127.37, 126.11, 125.62, 125.32, 62.42, 61.14, 40.38, 36.93, 21.49;
HRMS (ESI) m/z 508.1941 [M+H]$^+$ (calcd for C$_{32}$H$_{30}$NO$_3$S 508.1946, err −1.0 ppm);
HPLC analysis: 99% ee as determined by HPLC (CHIRALPAK IC, 90:10 Hexane/i-PrOH, 1.0 ml/min, 254 nm), t$_r$ $_{maj}$=42.6 min, t$_r$ $_{min}$=49.7 min;
IR v$_{max}$: 3314, 3055, 3026, 2922, 2851, 1710, 1599, 1493, 1445, 1398, 1327, 1153, 1090, 814, 762, 700, 665, 559, 548 cm$^{-1}$;
X-ray Crystallography see FIG. 4.

N-((1'S,2'R,3'S)-2'-formyl-4''-methyl-5'-phenyl-3',4'-dihydro-[1,1':3',1''-terphenyl]-1'(2'H)-yl)-4-methylbenzenesulfonamide (3b)

Colorless solid, m.p. 67~69° C., yield: 69 mg (66%); $[\alpha]^{20}_D$=−18.4 (c 1.09, CHCl$_3$);
$^1$H NMR (400 MHz, CDCl$_3$) δ 9.20 (d, J=1.6 Hz, 1H), 7.66 (d, J=8.3 Hz, 2H), 7.54 (dd, J=7.5, 1.8 Hz, 2H), 7.40-7.21 (m, 8H), 7.15-6.97 (m, 6H), 6.87 (s, 1H), 6.34 (t, J=1.7 Hz, 1H), 3.40 (dd, J=12.0, 1.7 Hz, 1H), 3.23 (td, J=11.3, 5.7 Hz, 1H), 2.59 (ddd, J=18.2, 10.8, 2.2 Hz, 1H), 2.36 (ddd, J=18.0, 5.8, 1.5 Hz, 1H), 2.29 (s, 6H);
$^{13}$C NMR (101 MHz, CDCl$_3$) δ 207.00, 144.56, 142.62, 140.16, 139.12, 139.06, 137.63, 137.37, 129.91, 129.19, 128.65, 128.40, 128.29, 127.56, 127.38, 126.13, 125.62, 125.32, 62.46, 61.21, 40.00, 37.03, 21.49, 21.10;
HRMS (ESI) m/z 522.2077 [M+H]$^+$ (calcd for C$_{33}$H$_{32}$NO$_3$S 522.2103, err −5.0 ppm);
HPLC analysis: 98% ee as determined by HPLC (CHIRALPAK IC, 80:20 Hexane/i-PrOH, 0.6 ml/min, 254 nm), t$_r$ $_{maj}$=35.2 min, t$_r$ $_{min}$=39.5 min;
IR v$_{max}$: 3325, 2924, 2851, 1715, 1597, 1514, 1491, 1445, 1329, 1153, 1090, 812, 758, 698, 662, 559 cm$^{-1}$.

N-((1'S,2'R,3'S)-2'-formyl-4''-methoxy-5'-phenyl-3',4'-dihydro-[1,1':3',1''-terphenyl]-1'(2'H)-yl)-4-methylbenzenesulfonamide (3c)

Colorless solid, m.p. 158~160° C., yield: 78 mg (73%); $[\alpha]^{20}_D$=−23.7 (c 1.30, CHCl$_3$);
$^1$H NMR (400 MHz, CDCl$_3$) δ 9.20 (d, J=1.6 Hz, 1H), 7.66 (d, J=8.3 Hz, 2H), 7.53 (d, J=7.5 Hz, 2H), 7.40-7.20 (m, 8H), 7.10 (d, J=8.6 Hz, 2H), 7.04 (d, J=8.1 Hz, 2H), 6.89 (s, 1H), 6.83 (d, J=8.6 Hz, 2H), 6.34 (t, J=1.8 Hz, 1H), 3.75 (s, 3H), 3.37 (dd, J=11.9, 1.8 Hz, 1H), 3.23 (td, J=11.3, 5.7 Hz, 1H), 2.58 (ddd, J=18.2, 10.7, 2.2 Hz, 1H), 2.37 (ddd, J=18.3, 5.9, 1.6 Hz, 1H), 2.29 (s, 3H);
$^{13}$C NMR (101 MHz, CDCl$_3$) δ 207.09, 158.96, 144.54, 142.63, 140.16, 139.18, 139.08, 132.53, 129.19, 128.68, 128.64, 128.40, 128.29, 127.56, 127.36, 126.11, 125.62, 125.33, 114.61, 62.50, 61.41, 55.37, 39.60, 37.05, 21.49;
HRMS (ESI) m/z 560.1874 [M+Na]$^+$ (calcd for C$_{33}$H$_{31}$NO$_4$NaS 560.1872, err 0.4 ppm);
HPLC analysis: 98% ee as determined by HPLC (CHIRALPAK IA, 90:10 Hexane/i-PrOH, 1.0 ml/min, 254 nm), t$_r$ $_{maj}$=28.1 min, t$_r$ $_{min}$=46.4 min;
IR v$_{max}$: 3312, 2951, 2918, 2849, 1709, 1609, 1597, 1510, 1495, 1443, 1402, 1331, 1246, 1182, 1153, 1090, 1030, 997, 839, 814, 773, 760, 698, 662, 561, 544, 530 cm$^{-1}$.

N-((1'S,2'R,3'S)-4''-chloro-2'-formyl-5'-phenyl-3',4'-dihydro-[1,1':3',1''-terphenyl]-1'(2'H)-yl)-4-methylbenzenesulfonamide (3d)

Colorless solid, m.p. 106~108° C., yield: 76 mg (70%); $[\alpha]^{20}_D$=−17.5 (c 1.11, CHCl$_3$);
$^1$H NMR (400 MHz, CDCl$_3$) δ 9.22 (d, J=1.6 Hz, 1H), 7.65 (d, J=8.3 Hz, 2H), 7.52 (d, J=7.3 Hz, 2H), 7.44-7.22 (m, 10H), 7.12 (d, J=8.4 Hz, 2H), 7.04 (d, J=8.0 Hz, 2H), 6.70 (s, 1H), 6.34 (t, J=1.8 Hz, 1H), 3.39 (dd, J=12.0, 1.7 Hz, 1H), 3.29 (ddd, J=12.1, 10.6, 5.8 Hz, 1H), 2.55 (ddd, J=18.1, 10.6, 2.2 Hz, 1H), 2.39 (ddd, J=18.1, 5.8, 1.6 Hz, 1H), 2.30 (s, 3H);
$^{13}$C NMR (101 MHz, CDCl$_3$) δ 206.38, 144.24, 142.77, 140.06, 139.47, 138.95, 138.89, 133.34, 129.38, 129.26, 129.08, 128.75, 128.46, 128.41, 127.73, 127.35, 126.05, 125.62, 125.39, 62.39, 61.15, 39.64, 36.80, 21.51;
HRMS (ESI) m/z 542.1547 [M+H]$^+$ (calcd for C$_{32}$H$_{29}$NO$_3$SCl 542.1557, err −1.8 ppm);
HPLC analysis: 98% ee as determined by HPLC (CHIRALPAK IA, 90:10 Hexane/i-PrOH, 1.0 ml/min, 254 nm), t$_r$ $_{maj}$=23.5 min, t$_r$ $_{min}$=37.6 min;
IR v$_{max}$: 3337, 2924, 1715, 1597, 1491, 1445, 1325, 1260, 1155, 1090, 1015, 814, 754, 698, 662, 559, 546 cm$^{-1}$.

N-((1'S,2'R,3'S)-4''-bromo-2'-formyl-5'-phenyl-3',4'-dihydro-[1,1':3',1''-terphenyl]-1'(2'H)-yl)-4-methylbenzenesulfonamide (3e)

Colorless solid, m.p. 110~112° C., yield: 100 mg (67%); $[\alpha]^{20}_D$=−9.9 (c 1.21, CHCl$_3$);
$^1$H NMR (400 MHz, CDCl$_3$) δ 9.22 (d, J=1.7 Hz, 1H), 7.65 (d, J=8.3 Hz, 2H), 7.52 (dd, J=7.2, 1.5 Hz, 2H), 7.42 (d, J=8.4 Hz, 2H), 7.39-7.20 (m, 8H), 7.10-7.00 (m, 4H), 6.67 (s, 1H), 6.34 (t, J=1.8 Hz, 1H), 3.39 (dd, J=12.1, 1.8 Hz, 1H), 3.28 (ddd, J=12.0, 10.6, 5.8 Hz, 1H), 2.54 (ddd, J=18.1, 10.6, 2.2 Hz, 1H), 2.39 (ddd, J=18.1, 5.8, 1.6 Hz, 1H), 2.30 (s, 3H);
$^{13}$C NMR (101 MHz, CDCl$_3$) δ 206.36, 144.23, 142.78, 140.07, 140.02, 138.93, 138.89, 132.36, 129.44, 129.27, 128.78, 128.48, 128.43, 127.76, 127.37, 126.06, 125.63, 125.42, 121.40, 62.38, 61.11, 39.72, 36.76, 21.53;
HRMS (ESI) m/z 586.1040 [M+H]$^+$ (calcd for C$_{32}$H$_{29}$NO$_3$SBr 586.1052, err −2.0 ppm);
HPLC analysis: 99% ee as determined by HPLC (CHIRALPAK IA, 90:10 Hexane/i-PrOH, 1.0 ml/min, 254 nm), t$_r$ $_{maj}$=24.6 min, t$_r$ $_{min}$=38.5 min;
IR v$_{max}$: 3318, 2924, 2851, 1715, 1597, 1489, 1445, 1395, 1325, 1155, 1090, 1009, 812, 758, 698, 660, 546 cm$^{-1}$.

N-((1'S,2'R,3'S)-2'-formyl-2"-methyl-5'-phenyl-3',4'-dihydro-[1,1':3',1"-terphenyl]-1'(2'H)-yl)-4-methylbenzenesulfonamide (3f)

Colorless solid, m.p. 68~70° C., yield: 45 mg (43%); $[\alpha]^{20}_D = -44.0$ (c 1.12, $CHCl_3$);
$^1$H NMR (400 MHz, $CDCl_3$) δ 9.20 (d, J=1.5 Hz, 1H), 7.66 (d, J=8.2 Hz, 2H), 7.56 (d, J=7.5 Hz, 2H), 7.37 (t, J=7.7 Hz, 2H), 7.33-7.22 (m, 7H), 7.18-7.07 (m, 3H), 7.01 (d, J=8.0 Hz, 2H), 6.87 (s, 1H), 6.39 (t, J=1.9 Hz, 1H), 3.69 (td, J=11.2, 5.8 Hz, 1H), 3.47 (d, J=11.8 Hz, 1H), 2.54 (ddd, J=18.4, 10.7, 2.1 Hz, 1H), 2.46-2.32 (m, 1H), 2.29 (s, 3H), 2.25 (s, 3H);
$^{13}$C NMR (101 MHz, $CDCl_3$) δ 207.22, 144.54, 142.54, 140.24, 139.47, 139.04, 138.96, 135.95, 131.08, 129.22, 128.73, 128.41, 128.36, 127.65, 127.31, 127.24, 126.90, 126.11, 126.04, 125.65, 125.26, 62.46, 61.26, 36.10, 34.73, 21.49, 20.03;
HRMS (ESI) m/z 522.2088 $[M+H]^+$ (calcd for $C_{33}H_{32}NO_3S$ 522.2103, err −2.9 ppm);
HPLC analysis: 96% ee as determined by HPLC (CHIRALPAK IF-3, 80:20 Hexane/i-PrOH, 0.6 ml/min, 254 nm), $t_{r\ maj}$=40.2 min, $t_{r\ min}$=28.2 min;
IR $v_{max}$: 3314, 2920, 2851, 1709, 1597, 1491, 1445, 1396, 1331, 1155, 1092, 812, 754, 696, 660, 557, 548 cm$^{-1}$.

N-((1'S,5'S,6'R)-6'-formyl-5'-(furan-2-yl)-5',6'-dihydro-[1,1':3',1"-terphenyl]-1'(4'H)-yl)-4-methylbenzenesulfonamide (3q)

Colorless solid, m.p. 77~79° C., yield: 58 mg (58%); $[\alpha]^{20}_D = -63.3$ (c 0.73, $CHCl_3$);
$^1$H NMR (400 MHz, $CDCl_3$) δ 9.20 (d, J=1.4 Hz, 1H), 7.63 (d, J=8.3 Hz, 2H), 7.51 (dd, J=8.3, 1.1 Hz, 2H), 7.38-7.21 (m, 9H), 7.03 (d, J=8.1 Hz, 2H), 6.85 (s, 1H), 6.34-6.24 (m, 2H), 6.08 (d, J=3.1 Hz, 1H), 3.45 (ddd, J=12.1, 10.3, 5.3 Hz, 1H), 3.39 (dd, J=11.8, 1.5 Hz, 1H), 2.76 (ddd, J=18.1, 10.3, 2.2 Hz, 1H), 2.39 (ddd, J=18.2, 5.4, 1.5 Hz, 1H), 2.30 (s, 3H);
$^{13}$C NMR (101 MHz, $CDCl_3$) δ 205.59, 153.63, 144.21, 142.72, 142.12, 140.08, 139.04, 138.78, 129.25, 128.65, 128.43, 128.36, 127.61, 127.33, 126.15, 125.67, 125.37, 110.53, 107.11, 62.14, 60.17, 33.64, 33.32, 21.51;
HRMS (ESI) m/z 520.1558 $[M+Na]^+$ (calcd for $C_{30}H_{27}NO_4SNa$ 520.1559, err −0.2 ppm);
HPLC analysis: 99% ee as determined by HPLC (CHIRALPAK IC, 85:15 Hexane/i-PrOH, 1.0 ml/min, 254 nm), $t_{r\ maj}$=29.4 min, $t_{r\ min}$=41.4 min;
IR $v_{max}$: 3312, 2922, 2853, 1717, 1597, 1541, 1495, 1447, 1327, 1157, 1090, 1011, 986, 814, 760, 698, 662, 565 cm$^{-1}$.

N-((1'S,5'S,6'R)-6'-formyl-5'-(naphthalen-2-yl)-5',6'-dihydro-[1,1':3',1"-terphenyl]-1'(4'H)-yl)-4-methylbenzenesulfonamide (3h)

Colorless solid, m.p. 170~172° C., yield: 74 mg (66%); $[\alpha]^{20}_D = +26.2$ (c 0.66, $CHCl_3$);
$^1$H NMR (400 MHz, $CDCl_3$) δ 9.21 (d, J=1.5 Hz, 1H), 7.84-7.73 (m, 3H), 7.71 (d, J=8.1 Hz, 2H), 7.60 (d, J=1.7 Hz, 1H), 7.57 (d, J=7.7 Hz, 2H), 7.52-7.40 (m, 2H), 7.40-7.33 (m, 3H), 7.32-7.24 (m, 6H), 7.08 (d, J=8.1 Hz, 2H), 6.89 (s, 1H), 6.39 (br. s, 1H), 3.54 (d, J=12.1 Hz, 1H), 3.47 (td, J=11.6, 11.0, 5.5 Hz, 1H), 2.73 (ddd, J=18.1, 10.4, 2.1 Hz, 1H), 2.47 (ddd, J=18.1, 5.6, 1.6 Hz, 1H), 2.31 (s, 3H);
$^{13}$C NMR (101 MHz, $CDCl_3$) δ 206.69, 144.53, 142.73, 140.23, 139.13, 139.08, 138.13, 133.62, 132.80, 129.30, 129.22, 128.73, 128.46, 128.37, 127.82, 127.69, 127.67, 127.45, 126.82, 126.74, 126.25, 126.17, 125.68, 125.50, 125.19, 62.48, 61.19, 40.57, 36.91, 21.56;
HRMS (ESI) m/z 558.2088 $[M+H]^+$ (calcd for $C_{36}H_{32}NO_3S$ 558.2103, err −2.7 ppm);
HPLC analysis: 98% ee as determined by HPLC (CHIRALPAK IC, 85:15 Hexane/i-PrOH, 1.0 ml/min, 254 nm), $t_{r\ maj}$=41.4 min, $t_{r\ min}$=34.1 min;
IR $v_{max}$: 3291, 2922, 2860, 1690, 1599, 1506, 1491, 1445, 1402, 1335, 1317, 1153, 1090, 816, 756, 702, 658, 571, 548 cm$^{-1}$.

N-((1'S,5'R,6'R)-6'-formyl-5'-((E)-styryl)-5',6'-dihydro-[1,1':3',1"-terphenyl]-1'(4'H)-yl)-4-methylbenzenesulfonamide (3i)

Colorless solid, m.p. 142~144° C., yield: 40 mg (38%); $[\alpha]^{20}_D = +25.1$ (c 0.51, $CHCl_3$);
$^1$H NMR (400 MHz, $CDCl_3$) δ 9.62 (d, J=1.7 Hz, 1H), 7.64 (d, J=8.3 Hz, 2H), 7.57-7.46 (m, 2H), 7.40-7.19 (m, 13H), 7.04 (d, J=8.0 Hz, 2H), 6.84 (s, 1H), 6.41 (d, J=15.7 Hz, 1H), 6.28 (t, J=1.8 Hz, 1H), 6.10 (dd, J=15.7, 9.0 Hz, 1H), 3.11 (dd, J=11.7, 1.8 Hz, 1H), 3.06-2.92 (m, 1H), 2.42 (ddd, J=18.0, 10.0, 2.2 Hz, 1H), 2.34-2.26 (m, 4H);
$^{13}$C NMR (101 MHz, $CDCl_3$) δ 206.70, 144.57, 142.66, 140.21, 139.22, 138.74, 136.33, 133.02, 129.26, 128.93, 128.80, 128.69, 128.46, 128.35, 128.06, 127.63, 127.39, 126.39, 126.16, 125.69, 125.55, 61.99, 61.20, 38.30, 34.70, 21.56;
HRMS (ESI) m/z 556.1923 $[M+Na]^+$ (calcd for $C_{34}H_{31}NO_3SNa$ 556.1922, err 0.2 ppm);
HPLC analysis: 97% ee as determined by HPLC (CHIRALPAK IF-3, 80:20 Hexane/i-PrOH, 0.6 ml/min, 254 nm), $t_{r\ maj}$=51.2 min, $t_{r\ min}$=63.9 min;
IR $v_{max}$: 3323, 2926, 2851, 1715, 1601, 1510, 1395, 1325, 1227, 1157, 1088, 989, 833, 814, 760, 702, 660, 557 cm$^{-1}$.

N-((1'S,5'S,6'R)-6'-formyl-5'-methyl-5',6'-dihydro-[1,1':3',1"-terphenyl]-1'(4'H)-yl)-4-methylbenzenesulfonamide (3j)

Colorless powder, m.p. 66~68° C., yield: 11 mg (12%); $[\alpha]^{20}_D = -132.7.3$ (c 0.49, $CHCl_3$);
$^1$H NMR (400 MHz, $CDCl_3$) δ 9.73 (d, J=2.0 Hz, 1H), 7.57 (d, J=8.3 Hz, 2H), 7.48 (d, J=7.7 Hz, 2H), 7.35 (t, J=7.7 Hz, 2H), 7.32-7.24 (m, 4H), 7.22-7.17 (m, 2H), 6.99 (d, J=8.0 Hz, 2H), 6.56 (s, 1H), 6.24 (t, J=1.8 Hz, 1H), 2.84 (dd, J=11.3, 2.1 Hz, 1H), 2.35 (tdq, J=11.0, 5.5, 5.1 Hz, 1H), 2.29 (s, 3H), 2.27 (ddd, J=17.9, 5.7, 1.6 Hz, 1H), 2.08 (ddd, J=17.9, 10.4, 2.2 Hz, 1H), 1.08 (d, J=6.5 Hz, 3H);
$^{13}$C NMR (101 MHz, $CDCl_3$) δ 207.88, 144.82, 142.48, 140.25, 139.55, 139.52, 129.20, 128.69, 128.38, 128.22, 127.62, 127.32, 126.17, 125.73, 125.69, 63.49, 62.23, 36.60, 28.71, 21.52, 19.26;
HRMS (ESI) m/z 446.1779 $[M+Na]^+$ (calcd for $C_{27}H_{28}NO_3S$ 446.1790, err −2.5 ppm);
HPLC analysis: 99% ee as determined by HPLC (CHIRALPAK ODH, 90:10 Hexane/i-PrOH, 0.6 ml/min, 254 nm), $t_{r\ maj}$=32.9 min, $t_{r\ min}$=38.4 min;
IR $v_{max}$: 3325, 2952, 2922, 2853, 1713, 1597, 1495, 1445, 1398, 1323, 1157, 1090, 1001, 814, 756, 698, 658, 546 cm$^{-1}$.

N-((1'S,2'R,3'S)-4-fluoro-5'-(4-fluorophenyl)-2'-formyl-3',4'-dihydro-[1,1':3',1''-terphenyl]-1'(2'H)-yl)-4-methylbenzenesulfonamide (3k)

Colorless solid, m.p. 99~101° C., yield: 48 mg (44%); $[\alpha]^{20}{}_D = -41.3$ (c 1.29, CHCl$_3$);
$^1$H NMR (400 MHz, CDCl$_3$) δ 9.20 (d, J=1.5 Hz, 1H), 7.65 (d, J=8.3 Hz, 2H), 7.50 (dd, J=8.9, 5.1 Hz, 2H), 7.32 (dd, J=8.1, 6.5 Hz, 2H), 7.27-7.18 (m, 5H), 7.10-6.97 (m, 6H), 6.88 (s, 1H), 6.28 (t, J=1.7 Hz, 1H), 3.37 (dd, J=12.0, 1.7 Hz, 1H), 3.27 (ddd, J=12.0, 10.6, 5.7 Hz, 1H), 2.60 (ddd, J=18.1, 10.7, 2.2 Hz, 1H), 2.43-2.31 (m, 4H);
$^{19}$F NMR (376 MHz, CDCl$_3$) δ −113.39, −115.12;
$^{13}$C NMR (101 MHz, CDCl$_3$) δ 206.69, 162.88 (d, J=248.2 Hz), 162.20 (d, J=247.0 Hz), 142.88, 140.41, 140.25 (d, J=3.1 Hz), 140.07, 138.26, 135.05 (d, J=3.3 Hz), 129.40, 129.30, 128.01 (d, J=8.2 Hz), 127.92 (d, J=9.5 Hz), 127.70, 127.37, 127.29, 125.21, 115.57 (d, J=21.6 Hz), 115.41 (d, J=21.4 Hz), 62.06, 61.20, 40.50, 37.08, 21.55;
HRMS (ESI) m/z 566.1573 [M+Na]$^+$ (calcd for C$_{32}$H$_{27}$NO$_3$F$_2$SNa 566.1577, err −0.7 ppm);
HPLC analysis: 98% ee as determined by HPLC (CHIRALPAK IC, 90:10 Hexane/i-PrOH, 1.0 ml/min, 254 nm), t$_{r\,maj}$=29.9 min, t$_{r\,min}$=35.7 min;
IR v$_{max}$: 3323, 2926, 2851, 1715, 1601, 1510, 1454, 1395, 1325, 1227, 1158, 1088, 989, 833, 814, 760, 702, 660, 557 cm$^{-1}$.

N-((1'S,2'R,3'S)-4-bromo-5'-(4-bromophenyl)-2'-formyl-3',4'-dihydro-[1,1':3',1''-terphenyl]-1'(2'H)-yl)-4-methylbenzenesulfonamide (3l)

Colorless solid, m.p. 125~127° C., yield: 86 mg (65%); $[\alpha]^{20}{}_D = -81.6$ (c 0.93, CHCl$_3$);
$^1$H NMR (400 MHz, CDCl$_3$) δ 9.18 (d, J=1.4 Hz, 1H), 7.64 (d, J=8.2 Hz, 2H), 7.49-7.44 (m, 3H), 7.43-7.38 (m, 3H), 7.32 (dd, J=8.0, 6.6 Hz, 2H), 7.28-7.22 (m, 1H), 7.19 (d, J=6.9 Hz, 2H), 7.11 (d, J=8.6 Hz, 2H), 7.08 (d, J=8.1 Hz, 2H), 6.88 (s, 1H), 6.30 (br. s, 1H), 3.35 (dd, J=12.0, 1.6 Hz, 1H), 3.26 (td, J=11.6, 11.2, 5.6 Hz, 1H), 2.60 (ddd, J=18.2, 10.6, 2.2 Hz, 1H), 2.40-2.29 (m, 4H);
$^{13}$C NMR (101 MHz, CDCl$_3$) δ 206.42, 143.47, 142.99, 140.21, 139.95, 138.44, 137.77, 131.83, 131.63, 129.43, 129.34, 128.03, 127.93, 127.67, 127.32, 127.20, 125.41, 122.60, 121.88, 62.10, 60.89, 40.38, 36.81, 21.57;
HRMS (ESI) m/z 664.0164 [M+H]$^+$ (calcd for C$_{32}$H$_{28}$NO$_3$SBr$_2$ 664.0157, err 1.1 ppm);
HPLC analysis: 96% ee as determined by HPLC (CHIRALPAK IB, 80:20 Hexane/i-PrOH, 0.8 ml/min, 254 nm), t$_{r\,maj}$=17.2 min, t$_{r\,min}$=10.4 min;
IR v$_{max}$: 3310, 2920, 2852, 1713, 1597, 1487, 1454, 1394, 1331, 1157, 1090, 1076, 1006, 814, 760, 702, 660, 557, 548 cm$^{-1}$.

N-((1S,2R,3S)-2-formyl-3,5-di(naphthalen-2-yl)-1,2,3,6-tetrahydro-[1,1'-biphenyl]-3-yl)-4-methylbenzenesulfonamide (3m)

Colorless solid, m.p. 126~128° C., yield: 55 mg (45%); $[\alpha]^{20}{}_D = -158.9$ (c 0.77, CHCl$_3$);
$^1$H NMR (300 MHz, CDCl$_3$) δ 9.24 (d, J=1.6 Hz, 1H), 8.09 (d, J=2.0 Hz, 1H), 7.94-7.75 (m, 6H), 7.70 (d, J=8.3 Hz, 2H), 7.65 (d, J=1.8 Hz, 1H), 7.61 (dd, J=8.7, 2.1 Hz, 1H), 7.58-7.46 (m, 5H), 7.39-7.30 (m, 2H), 7.30-7.18 (m, 3H), 7.00 (d, J=8.0 Hz, 2H), 6.97 (s, 1H), 6.60 (t, J=1.8 Hz, 1H), 3.62 (dd, J=12.0, 1.7 Hz, 1H), 3.39 (td, J=11.2, 5.8 Hz, 1H), 2.79 (ddd, J=18.1, 10.7, 2.1 Hz, 1H), 2.57 (ddd, J=18.1, 5.9, 1.5 Hz, 1H), 2.24 (s, 3H);
$^{13}$C NMR (101 MHz, CDCl$_3$) δ 206.82, 142.77, 141.71, 140.92, 140.17, 139.03, 136.22, 133.32, 133.29, 132.79, 129.38, 129.29, 128.71, 128.64, 128.33, 128.16, 127.81, 127.78, 127.73, 127.56, 127.51, 126.57, 126.49, 125.79, 125.37, 124.70, 124.06, 123.74, 62.71, 61.03, 40.52, 37.05, 21.50;
HRMS (ESI) m/z 630.2050 [M+Na]$^+$ (calcd for C$_{40}$H$_{33}$NO$_3$SNa 630.2079, err −4.6 ppm);
HPLC analysis: 99% ee as determined by HPLC (CHIRALPAK IC, 80:20 Hexane/i-PrOH, 0.8 ml/min, 254 nm), t$_{r\,maj}$=32.3 min, t$_{r\,min}$=42.1 min;
IR v$_{max}$: 3310, 2916, 2845, 1717, 1597, 1541, 1508, 1456, 1329, 1157, 1090, 858, 816, 748, 702, 556 cm$^{-1}$.

N-((1'S,2'R,3'S)-2'-formyl-5'-isobutyl-3',4'-dihydro-[1,1':3',1''-terphenyl]-1'(2'H)-yl)-4-methylbenzenesulfonamide (3n)

Colorless solid, m.p. 114~116° C., yield: 49 mg (50%); $[\alpha]^{20}{}_D = +78.1$ (c 0.63, CHCl$_3$);
$^1$H NMR (400 MHz, CDCl$_3$) δ 9.16 (d, J=1.6 Hz, 1H), 7.76 (d, J=8.3 Hz, 2H), 7.48 (dd, J=8.4, 1.3 Hz, 2H), 7.34 (dd, J=8.5, 6.9 Hz, 2H), 7.31-7.26 (m, 4H), 7.22 (ddt, J=9.5, 7.4, 3.5 Hz, 2H), 7.16-7.12 (m, 2H), 6.75 (s, 1H), 5.69 (s, 1H), 3.28 (dd, J=11.9, 1.7 Hz, 1H), 3.19 (ddd, J=11.9, 10.7, 5.6 Hz, 1H), 2.41 (s, 3H), 2.22 (ddd, J=18.1, 10.7, 2.2 Hz, 1H), 1.84-1.59 (m, 4H), 0.894 (d, J=6.2 Hz, 3H), 0.889 (d, J=6.2 Hz, 3H);
$^{13}$C NMR (101 MHz, CDCl$_3$) δ 207.08, 144.75, 142.67, 141.09, 140.89, 140.53, 129.21, 129.18, 128.61, 127.65, 127.54, 127.50, 127.47, 126.10, 124.23, 62.40, 61.87, 46.94, 40.37, 38.61, 25.93, 23.38, 22.04, 21.62;
HRMS (ESI) m/z 488.2250 [M+H]$^+$ (calcd for C$_{30}$H$_{34}$NO$_3$S 488.2259, err −1.8 ppm);
HPLC analysis: 99% ee as determined by HPLC (CHIRALPAK IA, 95:5 Hexane/i-PrOH, 0.6 ml/min, 254 nm), t$_{r\,maj}$=27.4 min, t$_{r\,min}$=47.7 min;
IR v$_{max}$: 3318, 2953, 2926, 2905, 2868, 1711, 1597, 1493, 1454, 1402, 1327, 1161, 1092, 1049, 991, 812, 760, 700, 660, 557, 544, 527, 519 cm$^{-1}$.

Methyl (1'S,2'R,3'S)-2'-formyl-1'-((4-methylphenyl)sulfonamido)-1',2',3',4'-tetrahydro-[1,1':3',1''-terphenyl]-5'-carboxylate (3o)

Colorless solid, m.p. 147~149° C., yield: 31 mg (32%); $[\alpha]^{20}{}_D = +3.5$ (c 1.19, CHCl$_3$);
$^1$H NMR (400 MHz, CDCl$_3$) δ 9.18 (d, J=1.6 Hz, 1H), 7.78 (d, J=8.1 Hz, 2H), 7.45 (d, J=7.5 Hz, 2H), 7.38 (t, J=7.6 Hz, 2H), 7.35-7.24 (m, 6H), 7.19 (d, J=6.8 Hz, 2H), 7.12 (t, J=2.1 Hz, 1H), 6.91 (s, 1H), 3.78 (s, 3H), 3.33 (dd, J=12.0, 1.6 Hz, 1H), 3.25 (td, J=11.7, 5.8 Hz, 1H), 2.48 (ddd, J=19.0, 10.5, 2.4 Hz, 1H), 2.41 (s, 3H), 2.36 (ddd, J=19.0, 5.8, 1.7 Hz, 1H);
$^{13}$C NMR (101 MHz, CDCl$_3$) δ 206.37, 166.26, 143.32, 142.91, 140.01, 139.78, 137.56, 132.64, 129.32, 129.24, 128.85, 128.02, 127.85, 127.71, 127.61, 126.02, 61.71, 60.81, 52.20, 39.89, 34.01, 21.63;
HRMS (ESI) m/z 490.1690 [M+H]$^+$ (calcd for C$_{28}$H$_{28}$NO$_5$S, 490.1688, err 0.4 ppm);
HPLC analysis: 99% ee as determined by HPLC (CHIRALPAK ADH, 80:10 Hexane/i-PrOH, 0.8 ml/min, 254 nm), t$_{r\,maj}$=25.7 min, t$_{r\,min}$=32.0 min;

IR $v_{max}$: 3314, 2951, 2845, 1717, 1647, 1599, 1495, 1335, 1263, 1157, 1092, 816, 762, 700, 662, 562, 548 cm$^{-1}$.

N-((1'R,2'S,3'R,4'S)-3'-formyl-4',6'-diphenyl-1',2',3',4'-tetrahydro-[1,1':2',1"-terphenyl]-4'-yl)-4-methylbenzenesulfonamide (3p)

Colorless powder, m.p. 124~126° C., yield: 19 mg (16%);
$[\alpha]^{20}_D$=−270.0 (c 0.50, CHCl$_3$);
$^1$H NMR (400 MHz, CDCl$_3$) δ 9.16 (d, J=1.7 Hz, 1H), 7.93 (d, J=8.3 Hz, 2H), 7.45 (dd, J=7.1, 1.6 Hz, 2H), 7.36-7.04 (m, 16H), 6.87 (t, J=7.4 Hz, 1H), 6.75 (t, J=7.6 Hz, 2H), 6.60 (d, J=1.9 Hz, 1H), 6.18 (dd, J=7.0, 1.4 Hz, 2H), 4.19 (dd, J=10.1, 2.1 Hz, 1H), 3.64 (dd, J=12.1, 1.8 Hz, 1H), 3.47 (dd, J=12.0, 10.0 Hz, 1H), 2.46 (s, 3H);
$^{13}$C NMR (101 MHz, CDCl$_3$) δ 206.48, 144.46, 143.14, 143.07, 140.70, 140.36, 138.76, 129.77, 129.53, 129.07, 128.89, 128.53, 128.06, 127.79, 127.59, 127.52, 127.45, 127.36, 126.96, 126.39, 126.18, 62.35, 61.87, 53.90, 49.41, 21.74;
HRMS (ESI) m/z 584.2250 [M+H]$^+$ (calcd for C$_{38}$H$_{34}$NO$_3$S 584.2259, err −1.5 ppm);
HPLC analysis: 94% ee as determined by HPLC (CHIRALPAK IC, 90:10 Hexane/i-PrOH, 1.0 ml/min, 254 nm), t$_r$ $_{maj}$=22.6 min, t$_r$ $_{min}$=28.7 min;
IR $v_{max}$: 3294, 3026, 2922, 2851, 1713, 1597, 1493, 1445, 1396, 1331, 1155, 1092, 814, 760, 698, 664, 565 cm$^{-1}$.

N-((1'S,2'R,3'S)-2'-formyl-5'-phenyl-3',4'-dihydro-[1,1':3',1"-terphenyl]-1'(2'H)-yl)-2-nitrobenzenesulfonamide (3q)

Colorless solid, m.p. 170~172° C., yield: 73 mg (68%);
$[\alpha]^{20}_D$=+125.2 (c 0.85, CHCl$_3$);
$^1$H NMR (400 MHz, CDCl$_3$) δ 9.23 (d, J=1.2 Hz, 1H), 7.79 (dd, J=8.0, 1.2 Hz, 1H), 7.68 (dd, J=7.9, 1.4 Hz, 1H), 7.63 (s, 1H), 7.60-7.50 (m, 3H), 7.38-7.31 (m, 7H), 7.30-7.24 (m, 3H), 7.24-7.17 (m, 3H), 7.14 (td, J=7.7, 1.3 Hz, 1H), 6.57 (t, J=1.8 Hz, 1H), 3.61-3.34 (m, 2H), 2.68 (ddd, J=18.2, 10.7, 2.1 Hz, 1H), 2.41 (ddd, J=18.1, 4.6, 1.7 Hz, 1H);
$^{13}$C NMR (101 MHz, CDCl$_3$) δ 206.27, 147.73, 144.13, 140.38, 139.14, 138.67, 135.88, 132.94, 132.12, 131.52, 129.30, 128.81, 128.73, 128.68, 127.87, 127.82, 127.77, 126.16, 125.88, 125.61, 124.61, 63.24, 61.14, 40.33, 36.33;
HRMS (ESI) m/z 539.1647 [M+H]$^+$ (calcd for C$_{31}$H$_{27}$N$_2$O$_5$S 539.1641, err 1.1 ppm);
HPLC analysis: 97% ee as determined by HPLC (CHIRALPAK ADH, 85:15 Hexane/i-PrOH, 0.8 ml/min, 254 nm), t$_r$ $_{maj}$=30.9 min, t$_r$ $_{min}$=22.9 min;
IR $v_{max}$: 3298, 2922, 2851, 1713, 1541, 1493, 1445, 1398, 1362, 1342, 1167, 854, 762, 698, 586, 554 cm$^{-1}$.

N-((1'S,2'R,3'S)-2'-formyl-5'-phenyl-3',4'-dihydro-[1,1':3',1"-terphenyl]-1'(2'H)-yl)-4-nitrobenzenesulfonamide (3r)

Colorless solid, m.p. 118~120° C., yield: 64 mg (59%);
$[\alpha]^{20}_D$=−13.6 (c 1.15, CHCl$_3$);
$^1$H NMR (400 MHz, CDCl$_3$) δ 9.21 (d, J=1.6 Hz, 1H), 8.05 (d, J=8.8 Hz, 2H), 7.93 (d, J=8.9 Hz, 2H), 7.51 (d, J=7.6 Hz, 2H), 7.39 (t, J=7.4 Hz, 2H), 7.35-7.24 (m, 8H), 7.27-7.15 (m, 4H), 6.38 (t, J=1.8 Hz, 1H), 3.45 (dd, J=12.0, 1.7 Hz, 1H), 3.25 (td, J=11.3, 6.0 Hz, 1H), 2.64 (dd, J=18.4, 10.7, 2.1 Hz, 1H), 2.47 (dd, J=18.4, 6.0, 1.6 Hz, 1H);
$^{13}$C NMR (101 MHz, CDCl$_3$) δ 207.38, 149.42, 148.55, 143.77, 140.01, 139.96, 138.23, 129.44, 128.97, 128.87, 128.77, 128.60, 127.99, 127.96, 127.64, 126.06, 125.42, 125.29, 123.87, 62.70, 60.84, 40.98, 36.59;
HRMS (ESI) m/z 539.1640 [M+H]$^+$ (calcd for C$_{31}$H$_{27}$N$_2$O$_5$S 539.1641, err −0.2 ppm);
HPLC analysis: 99% ee as determined by HPLC (CHIRALPAK IC, 80:20 Hexane/i-PrOH, 0.6 ml/min, 254 nm), t$_r$ $_{maj}$=38.6 min, t$_r$ $_{min}$=44.1 min;
IR $v_{max}$: 3306, 2924, 2851, 1713, 1605, 1530, 1495, 1341, 1163, 1090, 988, 854, 756, 743, 733, 696, 608, 554 cm$^{-1}$.

N-((1'S,2'R,3'S)-2'-(hydroxymethyl)-5'-phenyl-3',4'-dihydro-[1,1':3',1"-terphenyl]-1'(2'H)-yl)-P,P-diphenylphosphinic amide (3s)

Colorless solid, m.p. 244~246° C., yield: 38 mg (34%);
$[\alpha]^{20}_D$=−43.3 (c 0.76, CHCl$_3$);
$^1$H NMR (300 MHz, CDCl$_3$) δ 7.96 (ddd, J=11.8, 6.7, 3.1 Hz, 2H), 7.85 (ddd, J=12.0, 8.3, 1.5 Hz, 2H), 7.65 (d, J=7.4 Hz, 2H), 7.41-7.22 (m, 13H), 7.19-7.10 (m, 3H), 6.94 (dd, J=7.7, 2.1 Hz, 2H), 5.92 (s, 1H), 5.87 (d, J=8.4 Hz, 1H), 4.05 (ddd, J=12.1, 10.4, 6.1 Hz, 1H), 3.46 (dd, J=11.9, 5.2 Hz, 1H), 3.31 (dt, J=11.8, 3.8 Hz, 1H), 2.85-2.61 (m, 2H), 2.02 (dt, J=12.4, 2.3 Hz, 1H), 1.94 (s, 1H), 1.74 (t, J=5.1 Hz, 1H);
$^{31}$P NMR (121 MHz, CDCl$_3$) δ 18.63;
$^{13}$C NMR (75 MHz, CDCl$_3$) δ 148.06 (d, J=3.9 Hz), 144.22, 139.92, 138.37, 135.91 (d, J=129.7 Hz), 135.37 (d, J=129.7 Hz), 131.80 (d, J=9.2 Hz), 131.74 (d, J=9.6 Hz), 131.12 (d, J=2.3 Hz), 130.92 (d, J=2.6 Hz), 128.91, 128.38 (d, J=12.4 Hz), 128.233 (d, J=12.3 Hz), 128.23, 128.15, 127.85, 127.35, 126.74 (d, J=6.0 Hz), 126.60, 125.42, 63.45 (d, J=3.2 Hz), 60.54, 51.39 (d, J=2.9 Hz), 38.45, 37.52;
HRMS (ESI) m/z 556.2407 [M+H]$^+$ (calcd for C$_{37}$H$_{35}$NO$_2$P 556.2405, err 0.4 ppm);
HPLC analysis: 97% ee as determined by HPLC (CHIRALPAK IC, 90:10 Hexane/i-PrOH, 0.6 ml/min, 254 nm), t$_r$ $_{maj}$=15.5 min, t$_r$ $_{min}$=23.7 min;
IR $v_{max}$: 3183, 2914, 2880, 1599, 1489, 1435, 1194, 1109, 1070, 1055, 1030, 997, 976, 870, 760, 748, 739, 721, 691, 548, 534, 515 cm$^{-1}$.

(R)-5'-phenyl-1',6'-dihydro-[1,1':3',1"-terphenyl]-2'-carbaldehyde (4a)

Yellow oil, yield: 4% (2.7 mg);
$[\alpha]^{20}_D$=−81.4 (c 0.47, CHCl$_3$);
$^1$H NMR (400 MHz, CDCl$_3$) δ 9.70 (s, 1H), 7.53-7.41 (m, 7H), 7.39-7.29 (m, 5H), 7.22 (t, J=7.7 Hz, 2H), 7.16 (t, J=7.2 Hz, 1H), 6.67 (d, J=2.8 Hz, 1H), 4.46 (dd, J=9.4, 1.6 Hz, 1H), 3.29 (ddd, J=17.8, 9.4, 2.9 Hz, 1H), 3.15 (dd, J=17.8, 1.7 Hz, 1H);
$^{13}$C NMR (101 MHz, CDCl$_3$) δ 192.29, 153.71, 144.68, 142.96, 139.52, 137.56, 132.83, 129.37, 129.12, 129.09, 128.80, 128.62, 128.60, 127.37, 126.81, 125.98, 125.42, 35.01, 34.07;
HRMS (ESI) m/z 337.1582 [M+H]$^+$ (calcd for C$_{25}$H$_{21}$O 337.1592, err −3.0 ppm);
HPLC analysis: 93% ee as determined by HPLC (CHIRALPAK IC, 90:10 Hexane/i-PrOH, 1.0 ml/min, 254 nm), t$_r$ $_{maj}$=10.3 min, t$_r$ $_{min}$=18.1 min;
IR $v_{max}$: 2922, 2853, 1730, 1697, 1649, 1597, 1539, 1493, 1447, 1360, 1260, 1028, 756, 698 cm$^{-1}$.

(R)-4-bromo-5'-phenyl-1',6'-dihydro-[1,1':3',1"-terphenyl]-2'-carbaldehyde (4e)

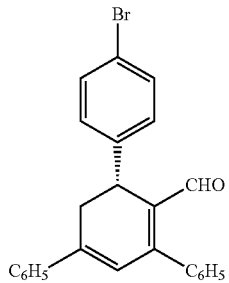

4e

Yellow oil, yield: 3% (2.7 mg);
$[\alpha]^{20}_D = -28.1$ (c 0.33, CHCl$_3$);
$^1$H NMR (400 MHz, CDCl$_3$) δ 9.68 (s, 1H), 7.51-7.39 (m, 7H), 7.39-7.33 (m, 5H), 7.22 (d, J=8.5 Hz, 2H), 6.67 (d, J=2.8 Hz, 1H), 4.40 (d, J=9.5 Hz, 1H), 3.28 (ddd, J=17.8, 9.4, 2.9 Hz, 1H), 3.10 (dd, J=17.8, 1.6 Hz, 1H);
$^{13}$C NMR (101 MHz, CDCl$_3$) δ 192.15, 153.84, 144.65, 142.02, 139.31, 137.34, 132.37, 131.72, 129.34, 129.29, 129.17, 128.90, 128.68, 125.98, 125.39, 120.68, 34.59, 33.86;
HRMS (ESI) m/z 415.0700 [M+H]$^+$ (calcd for C$_{25}$H$_{20}$OBr 415.0698, err 0.5 ppm);
HPLC analysis: 71% ee as determined by HPLC (CHIRALPAK IA, 95:5 Hexane/i-PrOH, 0.6 ml/min, 254 nm), t$_{r\,maj}$=13.3 min, t$_{r\,min}$=15.1 min;
IR v$_{max}$: 2922, 2853, 1734, 1697, 1647, 1541, 1489, 1446, 1260, 1074, 1009, 799, 762, 698 cm$^{-1}$.

(S)-5'-(furan-2-yl)-5',6'-dihydro-[1,1':3',1"-terphenyl]-4'-carbaldehyde (4g)

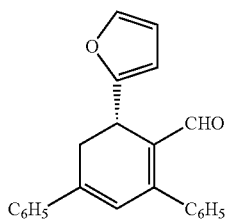

4g

Yellow oil, yield: 5.2% (3.4 mg);
$[\alpha]^{20}_D = -7.7$ (c 0.51, CHCl$_3$);
$^1$H NMR (400 MHz, CDCl$_3$) δ 9.72 (s, 1H), 7.55-7.51 (m, 2H), 7.48-7.43 (m, 3H), 7.42-7.33 (m, 5H), 7.28 (d, J=1.8 Hz, 1H), 6.61 (d, J=2.8 Hz, 1H), 6.20 (dd, J=3.2, 1.9 Hz, 1H), 5.98 (d, J=3.2 Hz, 1H), 4.56 (d, J=8.2 Hz, 1H), 3.35 (dd, J=17.6, 1.5 Hz, 1H), 3.05 (ddd, J=17.6, 8.4, 2.9 Hz, 1H);
$^{13}$C NMR (101 MHz, CDCl$_3$) δ 191.70, 155.20, 154.04, 145.19, 141.65, 139.47, 137.35, 130.56, 129.33, 129.20, 129.15, 128.84, 128.62, 126.12, 124.95, 110.14, 105.51, 30.98, 29.56;
HRMS (ESI) m/z 327.1393 [M+H]$^+$ (calcd for C$_{23}$H$_{19}$O$_2$ 327.1385, err 2.4 ppm);
HPLC analysis: 50% ee as determined by HPLC (CHIRALPAK IC, 90:10 Hexane/i-PrOH, 0.8 ml/min, 254 nm), t$_{r\,maj}$=15.3 min, t$_{r\,min}$=18.0 min;
IR v$_{max}$: 2924, 2853, 1651, 1599, 1541, 1495, 1447, 1360, 1260, 1198, 1103, 1090, 1080, 1024, 800, 760, 698 cm$^{-1}$.

Discussion

With 2a as a model unsaturated imine substrate, derivatives of cinnamaldehyde were tested as the enal substrates to provide compounds 3b-3f. Placing various substituents on the para position of the β-phenyl group of cinnamaldehyde were well tolerated, with the corresponding products obtained in 66-73% yields and excellent ee values (3b-3e). When a methyl unit was placed on the ortho-carbon of the β-phenyl ring of cinnamaldehyde, a longer reaction time was needed with a drop on product yield (3f, 43% yield) likely due to the steric hindrance. Changing the phenyl group into other heteroaryl (3g) and naphthyl (3h) substituents did not influence the reaction outcomes. The phenyl group of cinnamaldehyde could also be replaced by an alkene unit (3i). Aliphatic enal could give the desired product (3j) in a low yield (12%) even after an extended reaction time (24 h instead of 12 h).

The imine substrates (2) were subsequently examined using cinnamaldehyde (1a) as a model electrophile. Placing halogen substituents on the phenyl ring of the unsaturated imine substrates led to the corresponding products 3k and 3l with 44% and 65% yield respectively. The β-phenyl substituent of the unsaturated imine could be replaced by a naphthyl unit (3m). The β-aryl substituent of the imine can be changed to an alkyl (3n) or a carboxylic ester (3o) unit, albeit with yields decreased. The γ-phenyl substituted imine could give the desired product (3p) in a low yield (16%). Imines with other N-protecting groups were also investigated. Both 2- and 4-nitrobenzenesulfonyl protected imines (3q and 3r) were tolerated to give the corresponding products in 68% and 59% yield respectively. Interestingly, diphenylphosphinyl imine substrate also reacted fine to give 3s with 34% yield (isolated after reduction of the aldehyde to alcohol due to the instability of the amino aldehyde adduct). No desired product was observed when aldimine was employed as the substrate under the optimized reaction condition.

In all these catalytic reactions (3a-s), the cyclic β-amino aldehyde products were obtained as single diastereomers. The reaction likely gave trans-Mannich adduct that subsequently underwent an epimerization to the thermodynamically more stable isomer with excellent diastereoselectivity (see Example 4 for a detailed mechanistic discussion).

The reaction is amenable for scale up without loss in yields or ee values. Here, a preparation of 3a in 1.5 gram scale with 67% yield and 99% ee was demonstrated.

Example 3: Conversion of 3r to Unprotected Cyclic Amino Acid

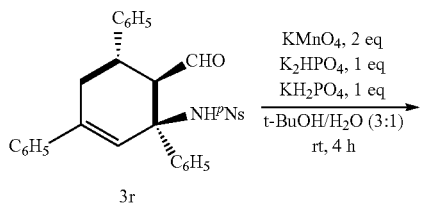

3r

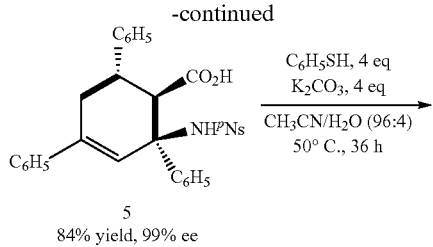

5
84% yield, 99% ee

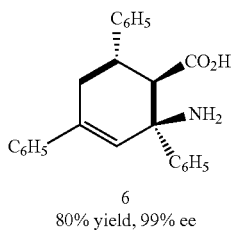

6
80% yield, 99% ee

Oxidation of 3r (*Tetrahedron Lett.* 1986, 27, 4537)

To the suspension solution of 3r (0.05 g, 0.1 mmol) in t-BuOH (3 mL) was added aqueous solution (1 mL) containing $KMnO_4$ (2 eq), $K_2HPO_4$ (1 eq), and $KH_2PO_4$ (1 eq) under air. The resulting mixture was then stirred at rt for 4 h. The reaction mixture was then diluted with brine and the organic layer was separated. The aqueous layer was extracted with EtOAc. The combined organic layer was dried over anhydrous $Na_2SO_4$, and the solvent was removed under decreased vacuum. The residue was subjected to silica gel column chromatography (DCM/MeOH 30:1) to obtain 5.

(1'S,2'R,3'S)-1'-((4-nitrophenyl)sulfonamido)-5'-phenyl-1',2',3',4'-tetrahydro-[1,1':3',1''-terphenyl]-2'-carboxylic Acid (5)

White powder, m.p. 131~133° C., yield: 46 mg (84%);

$[\alpha]^{20}_D$=−38.2 (c 0.69, $CHCl_3$);

$^1$H NMR (300 MHz, $CDCl_3$) δ 7.97 (d, J=8.8 Hz, 2H), 7.80 (d, J=8.8 Hz, 2H), 7.63-7.45 (m, 4H), 7.45-7.29 (m, 9H), 7.27-7.14 (m, 4H), 6.47 (d, J=1.9 Hz, 1H), 3.27 (td, J=11.1, 6.0 Hz, 1H), 3.10 (d, J=12.1 Hz, 1H), 2.52 (ddd, J=18.4, 10.7, 2.1 Hz, 1H), 2.37 (dd, J=18.6, 6.1 Hz, 1H);

$^{13}$C NMR (75 MHz, $CDCl_3$) δ 176.10, 149.26, 148.27, 143.49, 140.90, 140.16, 137.97, 128.95, 128.87, 128.83, 128.70, 128.42, 128.12, 127.85, 127.71, 125.74, 125.32, 124.74, 123.72, 62.15, 57.22, 40.95, 35.61;

HRMS (ESI) m/z 555.1596 $[M+H]^+$ (calcd for $C_{31}H_{27}N_2O_6S$ 555.1590, err 1.1 ppm);

HPLC analysis: 99% ee as determined by HPLC (CHIRALPAK IG-3, 75:25 Hexane/i-PrOH, 0.5 ml/min, 254 nm), $t_{r\ maj}$=30.5 min, $t_{r\ min}$=51.7 min;

IR $v_{max}$: 3650, 1715, 1697, 1593, 1530, 1495, 1447, 1348, 1161, 1090, 854, 760, 735, 700 cm$^{-1}$.

Deprotection of 5 (*ChemBioChem* 2004, 5, 1131; *Org. Biomol. Chem.* 2014, 12, 5827)

To the $CH_3CN$/DMSO (96:4; 1.5 mL) solution of 5 (0.03 g, 0.05 mmol) was added thiophenol (4 eq), potassium carbonate (4 eq) under nitrogen atmosphere. The resulting mixture was stirred at 50° C. for 36 h. The resulting mixture was directly loaded to flash chromatography (DCM/MeOH 10:1) to get 6.

(1'S,2'R,3'S)-1'-amino-5'-phenyl-1',2',3',4'-tetrahydro-[1,1':3',1''-terphenyl]-2'-carboxylic Acid (6)

White powder, m.p. 226~228° C., yield: 24 mg (80%);

$[\alpha]^{20}_D$=−24.8 (c 0.69, MeOH);

$^1$H NMR (400 MHz, DMSO-$d_6$) δ 8.58 (s, 2H), 7.50 (d, J=7.3 Hz, 2H), 7.44 (d, J=7.7 Hz, 2H), 7.39-7.22 (m, 10H), 7.17 (t, J=7.2 Hz, 1H), 6.10 (d, J=1.9 Hz, 1H), 3.54 (td, J=11.5, 5.2 Hz, 1H), 2.88 (d, J=12.4 Hz, 1H), 2.79 (ddd, J=17.6, 10.9, 2.3 Hz, 1H), 2.70 (dd, J=17.5, 5.4 Hz, 1H);

$^{13}$C NMR (101 MHz, DMSO-$d_6$) δ 173.06, 144.40, 143.25, 139.91, 137.81, 128.45, 128.15, 127.89, 127.78, 127.00, 126.28, 125.79, 125.38, 57.20, 56.95, 40.38, 36.30;

HRMS (ESI) m/z 370.1802 $[M+H]^+$ (calcd for $C_{25}H_{24}NO_2$ 370.1807, err −1.4 ppm);

HPLC analysis: 99% ee as determined by HPLC (CHIRALPAK IG-3, 75:25 Hexane/i-PrOH, 0.6 ml/min, 254 nm), $t_{r\ maj}$=19.9 min, $t_{r\ min}$=46.5 min;

IR $v_{max}$: 3456, 1636, 1570, 1558, 1495, 1447, 1373, 1236, 1190, 1028, 773, 758, 694, 540 cm$^{-1}$.

Discussion

As demonstrated above, the amino aldehyde adducts formed from Example 2 could be converted to the corresponding cyclic β-amino acids. As a technical note, it was easier to remove the nitrobenzenesulfonyl (nosyl, Ns) protecting group of the amine than the toluenesulfonyl (tosy, Ts) group. The aldehyde moiety of the Ns protected amino aldehyde 3r could be readily oxidized to the corresponding carboxylic acid (5) in 84% yield. The Ns group on the amino group could be removed in the presence of a thiophenol and base to give the unprotected amino acid (6) in 80% yield. In both transforming steps (from 3r to 5 and to 6), the optical purity of the products was not affected.

Example 4: Effect of NaCl for Facilitating Formation of 3a Over 4a

To investigate the effect of NaCl, compound 3a was subjected to the conditions of General Procedure 1 with the changes shown in Table 3 below.

As shown in Table 3 (entries 1 and 3), 4a was transformed from 3a via simple elimination of $TsNH_2$, with ee value remained (entries 3 and 4). The formation of by-product 4a can be suppressed by the NaCl salt additive (entry 1 vs 2; entry 3 vs 4). It appears that the NaCl salt additive may facilitate the precipitation of product 3a and thus suppress its transformation to 4a.

Table 3

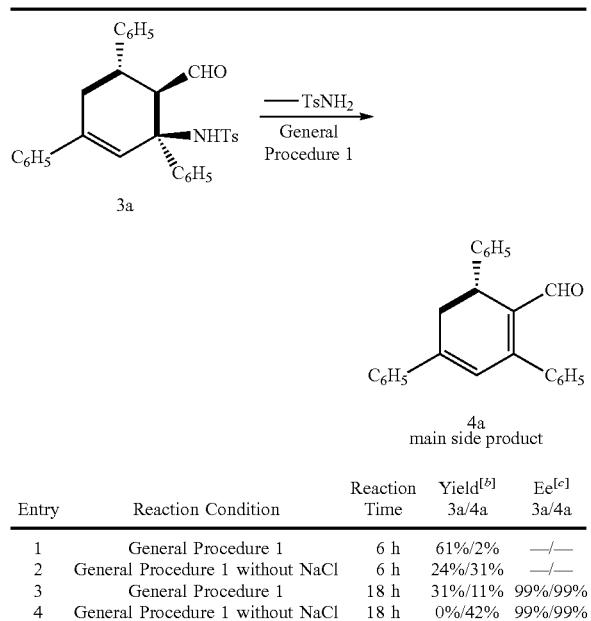

| Entry | Reaction Condition | Reaction Time | Yield[b] 3a/4a | Ee[c] 3a/4a |
|---|---|---|---|---|
| 1 | General Procedure 1 | 6 h | 61%/2% | —/— |
| 2 | General Procedure 1 without NaCl | 6 h | 24%/31% | —/— |
| 3 | General Procedure 1 | 18 h | 31%/11% | 99%/99% |
| 4 | General Procedure 1 without NaCl | 18 h | 0%/42% | 99%/99% |

[a]Reaction procedure was same to the catalytic procedure illustrated in General Procedure 1.
[b]NMR yield based on 3a using trimethoxylbenzene as internal standard.
[c]Enantiomeric excess of 3a was determined via HPLC analysis on stationary chiral phase.

Example 5: Reaction Pathway for Formation of by-Product 4a

Corresponding enones, derived from hydrolysis of imine substrates, may undergo the same transformations as those of imine substrates to give the main side product. Thus, a control experiment employing 2a' (corresponding enone of 2a) and 1a as substrates was performed following General Procedure 1, except using 2a' instead of imine 2a (FIG. 5).

Only trace amount of 4a can be observed from the catalytic reaction between enal 1a and the enone substrate 2a'. The Michael addition product 3a' and the cyclic alcohol 3a" were observed as the main products instead of 4a in the reaction of 1a and 2a', indicative of the impossibility of main side product formation through imine hydrolysis pathway under established model condition.

(E)-7-oxo-3,5,7-triphenylhept-5-enal (3a')

Colorless oil, yield: 21% (15 mg);
$^1$H NMR (400 MHz, CDCl$_3$) δ 9.59 (t, J=1.9 Hz, 1H), 7.85 (d, J=7.3 Hz, 2H), 7.54 (t, J=7.4 Hz, 1H), 7.47-7.35 (overlap, 7H), 7.18-7.11 (m, 2H), 7.10-7.04 (overlap, 3H), 6.99 (s, 1H), 3.57 (dd, J=13.3, 7.6 Hz, 1H), 3.49 (dd, J=13.3, 7.9 Hz, 1H), 3.35 (p, J=7.5 Hz, 1H), 2.82 (dt, J=6.8, 1.5 Hz, 2H);
$^{13}$C NMR (101 MHz, CDCl$_3$) δ 201.74, 191.80, 156.87, 143.02, 141.31, 139.20, 132.78, 129.28, 128.88, 128.61, 128.58, 128.41, 127.69, 127.13, 126.83, 125.18, 49.55, 39.46, 37.42;
HRMS (ESI) m/z 355.1697 [M+H]$^+$ (calcd for C$_{25}$H$_{23}$O$_2$ 355.1698, err −0.3 ppm);
IR $v_{max}$: 2922, 1720, 1653, 1599, 1570, 1491, 1446, 1215, 760, 698 cm$^{-1}$.

(1'S,2'R,3'S)-1'-hydroxy-5'-phenyl-1',2',3',4'-tetrahydro-[1,1':3',1''-terphenyl]-2'-carbaldehyde (3a")

Colorless solid, m.p. 61~63° C., yield: 6 mg (9%);
$[α]^{20}_D$=−38.1 (c 0.85, CHCl$_3$);
$^1$H NMR (400 MHz, CDCl$_3$) δ 9.50 (d, J=3.3 Hz, 1H), 7.52-7.43 (m, 4H), 7.40-7.35 (m, 3H), 7.34-7.29 (m, 6H), 7.27-7.21 (m, 2H), 6.15 (dd, J=2.3, 1.1 Hz, 1H), 3.83 (td, J=11.9, 5.1 Hz, 1H), 3.23 (dd, J=12.3, 3.3 Hz, 1H), 3.02 (s, 1H), 2.98 (ddd, J=17.9, 5.1, 1.2 Hz, 1H), 2.79 (ddd, J=17.9, 11.5, 2.4 Hz, 1H);
$^{13}$C NMR (101 MHz, CDCl$_3$) δ 204.60, 145.81, 142.07, 139.99, 139.78, 129.14, 128.78, 128.68, 128.63, 128.36, 127.94, 127.59, 127.40, 125.79, 125.54, 75.29, 61.97, 39.60, 37.55;
HRMS (ESI) m/z 355.1693 [M+H]$^+$ (calcd for C$_{25}$H$_{23}$O$_2$ 355.1698, err −1.4 ppm);
HPLC analysis: 96% ee as determined by HPLC (CHIRALPAK IC-3, 95:5 Hexane/i-PrOH, 0.4 ml/min, 254 nm), $t_{r\ maj}$=66.7 min, $t_{r\ min}$=63.8 min;
IR $v_{max}$: 3462, 2916, 1717, 1599, 1493, 1447, 1074, 1028, 754, 700 cm$^{-1}$.

Example 6: Effect of Reaction Time on Transformation Between Diastereoisomers 3a"-A and 3a"-B As discussed in Example 5, the cyclization product 3a" was obtained when using enone 2a' as the substrate, consisting of diastereoisomers 3a"-A and 3a"-B. It is found that the dr values of 3a"-A and 3a"-B are varied from 1:1 to 5:1 depending on the reaction time (FIG. 6). An enolization process under basic condition may account for the observed phenomenon.

Example 7: Electron-Donating Groups on Imine Substrate LED to Catalyst Deactivation

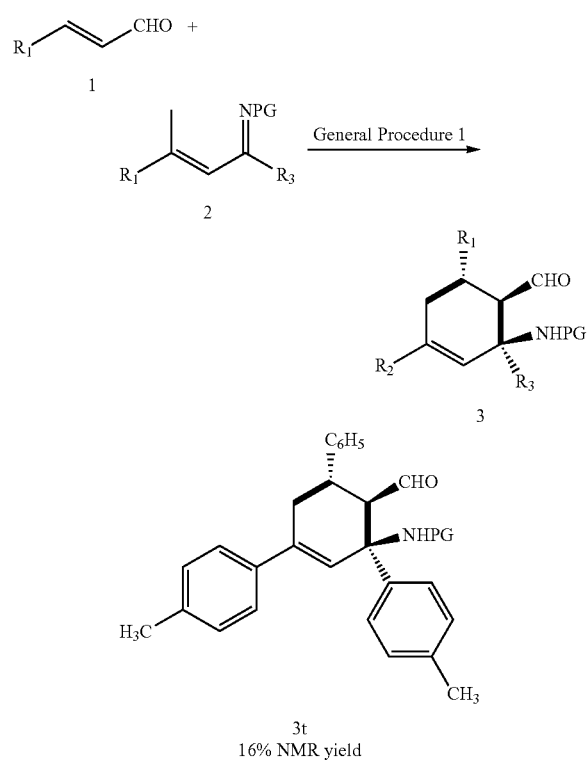

-continued

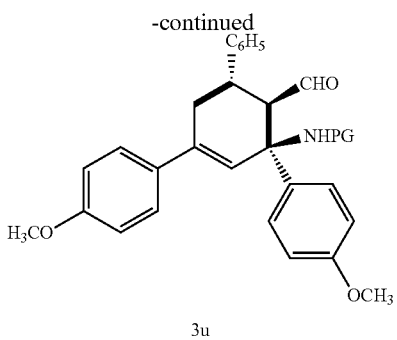

3u
0% yield

During the examination of imine substrates following General Procedure 1 (with any variations specified hereinbelow), the yield of desired product decreased a lot when $R^2$, $R^3$ (these R groups refer to those in the scheme directly above this text) were electron-donating groups such as 4-toluene substituent (3t) (16% yield). More electron-rich groups such as 4-anisole substituent did not give any corresponding product (3u).

An experiment was then performed using 2m as substrate following General Procedure 1 except for 1 equivalent loading of the catalyst, which led to identification of catalyst deactivation product 7 (FIG. 7).

(S,Z)—N-((2-(diphenyl((trimethylsilyl)oxy)methyl) pyrrolidin-1-yl)methylene)-4-methylbenzenesulfonamide (7)

Yellowish white solid, m.p. 197~199° C., yield: 40 mg (80%);

$[\alpha]^{20}_D$=−130.2 (c 0.94, CHCl$_3$);

$^1$H NMR (400 MHz, CDCl$_3$) δ 8.52 (s, 1H), 7.79 (d, J=8.3 Hz, 2H), 7.37 (s, 5H), 7.33-7.21 (m, 7H), 4.79 (dd, J=9.3, 3.5 Hz, 1H), 3.46 (ddd, J=13.8, 8.9, 5.9 Hz, 1H), 2.43 (s, 3H), 2.23 (dddd, J=14.8, 12.8, 8.9, 6.6 Hz, 2H), 1.98 (ddt, J=13.6, 8.9, 4.4 Hz, 1H), 1.53 (dddd, J=15.7, 9.7, 8.1, 5.3 Hz, 1H), 1.14-0.98 (m, 1H), −0.18 (s, 9H);

$^{13}$C NMR (101 MHz, CDCl$_3$) δ 158.36, 142.19, 141.48, 140.63, 140.28, 129.47, 129.25, 128.62, 128.47, 128.10, 127.76, 126.68, 83.52, 69.71, 47.48, 27.47, 22.30, 21.63, 1.76;

HRMS (ESI) m/z 507.2129 [M+H]$^+$ (calcd for C$_{28}$H$_{35}$N$_2$O$_3$SSi 507.2138, err −1.8 ppm);

IR $\nu_{max}$ 2961, 2886, 1602, 1494, 1446, 1354, 1300, 1252, 1146, 1090, 1053, 928, 866, 816, 756, 714, 704, 664, 561 cm$^{-1}$.

Proposed Mechanism

The proposed reaction mechanism for the generation of the cis-Mannich products is depicted in FIG. 3. The α,β-unsaturated iminium intermediate 1 reacts with the dienamine intermediate 2 to form the vinylogous Michael adduct I, which leads to intermediate III through an intramolecular trans-Mannich reaction. Hydrolysis of intermediate III gives diastereoisomer 3', which can epimerize to the thermodynamically more stable product 3 through an enolization process under basic conditions. This epimerization process has been well documented in literature (e.g., *Tetrahedron Lett.* 1997, 38, 8849-8852). Hydrogen bond between —NHTs and —CHO may accelerate this isomerization process.

The invention claimed is:

1. A method of forming a compound of formula I:

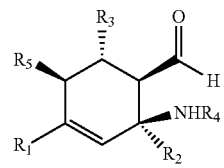

where:

$R_1$ and $R_2$ each independently represent $R_{6a}OC(O)$—, $C_1$ to $C_{10}$ alkyl, a carbocyclic ring system, and a heterocyclic ring system, where the $C_1$ to $C_{10}$ alkyl, carbocyclic ring system and heterocyclic ring system are unsubstituted or substituted by one or more substituents selected from the group consisting of halo, $OR_{7a}$, aryl, Het$^a$, and $C_1$ to $C_6$ alkyl, which $C_1$ to $C_6$ alkyl and aryl are unsubstituted or substituted by one or more halo groups;

$R_3$ represents $C_1$ to $C_{10}$ alkyl, $C_2$ to $C_{10}$ alkenyl, a carbocyclic ring system, and a heterocyclic ring system, where the $C_1$ to $C_{10}$ alkyl, $C_2$ to $C_{10}$ alkenyl, carbocyclic ring system and heterocyclic ring system are unsubstituted or substituted by one or more substituents selected from the group consisting of halo, $OR_{7b}$, aryl, Het$^b$, and $C_1$ to $C_6$ alkyl, which $C_1$ to $C_6$ alkyl and aryl are unsubstituted or substituted by one or more halo groups;

$R_4$ represents a nitrogen protecting group;

$R_5$ represents H, $R_{6b}OC(O)$—, $C_1$ to $C_{10}$ alkyl, a carbocyclic ring system, and a heterocyclic ring system, where the $C_1$ to $C_{10}$ alkyl, carbocyclic ring system and heterocyclic ring system are unsubstituted or substituted by one or more substituents selected from the group consisting of halo, $OR_{7c}$, aryl, Het$^c$, and $C_1$ to $C_6$ alkyl, which $C_1$ to $C_6$ alkyl and aryl are unsubstituted or substituted by one or more halo groups;

Het$^a$ to Het$^c$ are each independently a 4- to 14-membered heterocyclic ring system that is unsubstituted or substituted with one or more substituents selected from halo and $C_1$ to $C_6$ alkyl, which is unsubstituted or substituted by one or more halo groups;

$R_{6a}$ and $R_{6b}$ and $R_{7a}$ to $R_{7c}$ are each independently $C_1$ to $C_{10}$ alkyl that is unsubstituted or substituted by one or more halo groups;

comprising the steps of reacting a compound of formula II:

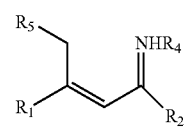

where $R_1$, $R_2$, $R_4$ and $R_5$ are as defined above, with a compound of formula III:

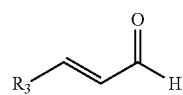

where $R_3$ is as defined above, in the presence of a solvent, a base comprising $KH_2PO_4$, and a catalyst of formula IV:

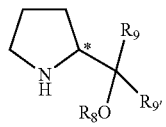

where:
the * represents a chiral centre;
$R_8$ is a protecting group for OH; and
$R_9$ and $R_{9'}$ each independently represent an aryl group that is unsubstituted or substituted by one or more groups selected from halo, $C_1$ to $C_6$ alkyl, phenyl, and naphthyl, where the $C_1$ to $C_6$ alkyl, phenyl and naphthyl are unsubstituted or substituted by one or more halo groups, optionally wherein $R_9$ and $R_{9'}$ are identical.

2. The method according to claim 1, wherein $R_1$ and $R_2$ each independently represent $R_{6a}OC(O)$—, $C_1$ to $C_6$ alkyl, phenyl, and naphthyl, where the $C_1$ to $C_6$ alkyl, phenyl, and naphthyl are unsubstituted or substituted by one or more substituents selected from the group consisting of halo and $C_1$ to $C_3$ alkyl, which $C_1$ to $C_3$ alkyl is unsubstituted or substituted by one or more halo groups.

3. The method according to claim 1, wherein $R_5$ represents H, $C_1$ to $C_6$ alkyl, and phenyl, where the $C_1$ to $C_6$ alkyl and phenyl are unsubstituted or substituted by one or more substituents selected from the group consisting of halo and $C_1$ to $C_3$ alkyl, which $C_1$ to $C_3$ alkyl is unsubstituted or substituted by one or more halo groups.

4. The method according to claim 1, wherein $R_3$ represents $C_1$ to $C_6$ alkyl, $C_2$ to $C_6$ alkenyl, phenyl, naphthyl and furanyl, where the $C_1$ to $C_6$ alkyl, $C_2$ to $C_6$ alkenyl, phenyl, naphthyl and furanyl are unsubstituted or substituted by one or more substituents selected from the group consisting of halo, phenyl, $OC_1$ to $C_3$ alkyl and $C_1$ to $C_3$ alkyl, which phenyl, $OC_1$ to $C_3$ alkyl and $C_1$ to $C_3$ alkyl are unsubstituted or substituted by one or more halo groups.

5. The method according to claim 1, wherein $R_4$ is selected from a tosyl group, a nosyl group, and a diphenylphosphinyl group and suitable isomers thereof.

6. The method according to claim 1, wherein $R_{6a}$ and $R_{6b}$ and $R_{7a}$ to $R_{7c}$ are each independently $C_1$ to $C_3$ alkyl that is unsubstituted or substituted by one or more halo groups.

7. The method according to claim 1, wherein the catalyst of formula IV is:

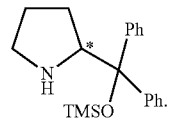

8. The method according to claim 1, wherein the base further comprises a further base selected from one or more of the group consisting of $K_2HPO_4$, an amine base, and $Na_2HPO_4$.

9. The method according to claim 8, wherein the amine base is selected from one or more of the group consisting of $Et_3N$, DMAP, and DABCO.

10. The method according to claim 8, wherein a total molar ratio of the base comprising $KH_2PO_4$ and a further base relative to the compound of formula II is from 1.5:1 to 2:1, where the $KH_2PO_4$ and the further base have a molar ratio of 1:1.

11. The method according to claim 1, wherein the reaction is conducted in the presence of an additive selected from one or more of the group consisting of LiBr, NaCl, KCl, and $MgCl_2$.

12. The method according to claim 11, wherein the additive is NaCl.

13. The method according to claim 11, wherein a molar ratio of the additive to the compound of formula II is about 1:1.

14. The method according to claim 1, wherein the solvent consists essentially of an alkyl alcohol and water.

15. The method according to claim 14, wherein the solvent is methanol and water.

16. The method according to claim 14, wherein the alkyl alcohol:water volume:volume ratio is from 90:10 to 99.5:0.5.

17. The method according to claim 16, wherein the alkyl alcohol:water volume:volume ratio is 99:1.

18. The method according to claim 1, wherein one or both of the following apply:
    (a) the reaction is conducted at a temperature of from 40 to 80° C.; and
    (b) the reaction time is from 6 to 24 hours.

19. The method according to claim 1, wherein one or more of the following apply:
    (a) a molar ratio of the compound of formula III to the compound of formula II is from 1.1:1 to 4:1;
    (b) a molar ratio of $KH_2PO_4$ to the compound of formula II is from 0.1:1 to 5:1; and
    (c) a molar ratio of the catalyst of formula IV to the compound of formula II is from 0.2:1 to 0.4:1.

* * * * *